United States Patent
Shanley et al.

(10) Patent No.: US 8,187,321 B2
(45) Date of Patent: May 29, 2012

(54) EXPANDABLE MEDICAL DEVICE FOR DELIVERY OF BENEFICIAL AGENT

(75) Inventors: John F. Shanley, Redwood City, CA (US); Neal L. Eigler, Pacific Palisades, CA (US); Kinam Park, West Lafayette, IN (US); Elazer R. Edelman, Brookline, MA (US)

(73) Assignee: Innovational Holdings, LLC, New Brunswick, NJ (US)

( * ) Notice: Subject to any disclaimer, the term of this patent is extended or adjusted under 35 U.S.C. 154(b) by 825 days.

(21) Appl. No.: 11/222,202

(22) Filed: Sep. 7, 2005

(65) Prior Publication Data

US 2006/0009838 A1   Jan. 12, 2006

Related U.S. Application Data

(63) Continuation of application No. 10/729,631, filed on Dec. 5, 2003, now abandoned, which is a continuation of application No. 09/948,989, filed on Sep. 7, 2001, now Pat. No. 7,208,010.

(60) Provisional application No. 60/314,259, filed on Aug. 20, 2001.

(51) Int. Cl.
  *A61F 2/06* (2006.01)

(52) U.S. Cl. ............... 623/1.42; 623/1.44; 623/1.46; 427/2.24

(58) Field of Classification Search ........ 623/1.42–1.46, 623/1.15–1.17, 1.39; 427/2.24, 2.25
See application file for complete search history.

(56) References Cited

U.S. PATENT DOCUMENTS

| | | | |
|---|---|---|---|
| 3,657,744 A | 4/1972 | Ersek |
| 4,300,244 A | 11/1981 | Bokros |
| 4,531,936 A | 7/1985 | Gordon |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |

(Continued)

FOREIGN PATENT DOCUMENTS

CA    2234787 A1    4/1998

(Continued)

OTHER PUBLICATIONS

Jennifer L. West, "Drug Delivery—Pulsed Polymers." Nature Materials, vol. 2, Nov. 2003, pp. 709-710.

(Continued)

*Primary Examiner* — David H Willse
*Assistant Examiner* — Javier Blanco

(57) ABSTRACT

An expandable medical device has a plurality of elongated struts joined together to form a substantially cylindrical device which is expandable from a cylinder having a first diameter to a cylinder having a second diameter. At least one of the plurality of struts includes at least one opening extending at least partially through a thickness of said strut. A beneficial agent is loaded into the opening within the strut in layers to achieve desired temporal release kinetics of the agent. Alternatively, the beneficial agent is loaded in a shape which is configured to achieve the desired agent delivery profile. A wide variety of delivery profiles can be achieved including zero order, pulsatile, increasing, decrease, sinusoidal, and other delivery profiles.

19 Claims, 9 Drawing Sheets

U.S. PATENT DOCUMENTS

| | | |
|---|---|---|
| 4,824,436 A | 4/1989 | Wolinsky |
| 4,834,755 A | 5/1989 | Silvestrini et al. |
| 4,889,119 A | 12/1989 | Jamiolkowski et al. |
| 4,916,193 A | 4/1990 | Tang et al. |
| 4,955,878 A | 9/1990 | See et al. |
| 4,957,508 A | 9/1990 | Kaneko et al. |
| 4,960,790 A | 10/1990 | Steela et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |
| 5,017,381 A | 5/1991 | Maruyama et al. |
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,178 A | 10/1991 | Ya et al. |
| 5,059,211 A | 10/1991 | Stack et al. |
| 5,078,726 A | 1/1992 | Kreamer |
| 5,085,629 A | 2/1992 | Goldberg et al. |
| 5,092,841 A | 3/1992 | Spears |
| 5,102,417 A | 4/1992 | Palmaz |
| 5,139,480 A | 8/1992 | Hickle et al. |
| 5,157,049 A | 10/1992 | Haugwitz et al. |
| 5,160,341 A | 11/1992 | Brenneman et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,223,092 A | 6/1993 | Grinnell et al. |
| 5,234,456 A | 8/1993 | Silvestrini |
| 5,242,399 A | 9/1993 | Lau et al. |
| 5,282,823 A | 2/1994 | Schwartz et al. |
| 5,283,257 A | 2/1994 | Gregory et al. |
| 5,286,254 A | 2/1994 | Shapland et al. |
| 5,288,711 A | 2/1994 | Mitchell et al. |
| 5,290,271 A | 3/1994 | Jernberg |
| 5,292,512 A | 3/1994 | Schaefer et al. |
| 5,304,121 A | 4/1994 | Sahatjian |
| 5,314,688 A | 5/1994 | Kauffman et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso |
| 5,439,446 A | 8/1995 | Barry |
| 5,439,466 A | 8/1995 | Kilejian |
| 5,439,686 A | 8/1995 | Desai et al. |
| 5,441,515 A | 8/1995 | Khosravi et al. |
| 5,441,745 A | 8/1995 | Presant et al. |
| 5,443,458 A | 8/1995 | Eury |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,382 A | 9/1995 | Dayton |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,472,985 A | 12/1995 | Grainger et al. |
| 5,473,055 A | 12/1995 | Mongelli et al. |
| 5,496,365 A | 3/1996 | Sgro |
| 5,499,373 A | 3/1996 | Richards et al. |
| 5,500,013 A | 3/1996 | Buscemi et al. |
| 5,510,077 A | 4/1996 | Dinh et al. |
| 5,512,055 A | 4/1996 | Domb et al. |
| 5,516,781 A | 5/1996 | Morris et al. |
| 5,519,954 A | 5/1996 | Garrett |
| 5,523,092 A | 6/1996 | Hanson et al. |
| 5,527,344 A | 6/1996 | Arzbaecher et al. |
| 5,534,287 A | 7/1996 | Lukic |
| 5,545,208 A | 8/1996 | Wolff et al. |
| 5,545,210 A | 8/1996 | Hess et al. |
| 5,545,569 A | 8/1996 | Grainger et al. |
| 5,551,954 A | 9/1996 | Buscemi et al. |
| 5,554,182 A | 9/1996 | Dinh et al. |
| 5,556,413 A | 9/1996 | Lam |
| 5,562,922 A | 10/1996 | Lambert |
| 5,563,146 A | 10/1996 | Morris et al. |
| 5,571,089 A | 11/1996 | Crocker |
| 5,571,166 A | 11/1996 | Dinh et al. |
| 5,575,571 A | 11/1996 | Takebayashi et al. |
| 5,578,075 A | 11/1996 | Dayton |
| 5,591,224 A | 1/1997 | Schwartz et al. |
| 5,591,227 A | 1/1997 | Dinh et al. |
| 5,593,434 A | 1/1997 | Williams |
| 5,595,722 A | 1/1997 | Grainger et al. |
| 5,599,352 A | 2/1997 | Dinh et al. |
| 5,599,722 A | 2/1997 | Sugisaka et al. |
| 5,599,844 A | 2/1997 | Grainger et al. |
| 5,605,696 A | 2/1997 | Eury et al. |
| 5,607,442 A | 3/1997 | Fischell et al. |
| 5,607,463 A | 3/1997 | Schwartz et al. |
| 5,607,475 A | 3/1997 | Cahalan et al. |
| 5,609,626 A | 3/1997 | Quijano et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,785 A | 5/1997 | Schwartz et al. |
| 5,628,787 A | 5/1997 | Mayer |
| 5,629,077 A | 5/1997 | Turnlund et al. |
| 5,632,840 A | 5/1997 | Campbell |
| 5,637,113 A | 6/1997 | Tartaglia et al. |
| 5,643,314 A | 7/1997 | Carpenter et al. |
| 5,646,160 A | 7/1997 | Morris et al. |
| 5,649,977 A | 7/1997 | Campbell |
| 5,651,174 A | 7/1997 | Schwartz et al. |
| 5,660,873 A | 8/1997 | Nikolaychik et al. |
| 5,665,591 A | 9/1997 | Sonenshein et al. |
| 5,667,764 A | 9/1997 | Kopia et al. |
| 5,670,161 A | 9/1997 | Healy et al. |
| 5,670,659 A | 9/1997 | Alas et al. |
| 5,674,241 A | 10/1997 | Bley et al. |
| 5,674,242 A | 10/1997 | Phan et al. |
| 5,674,278 A | 10/1997 | Boneau |
| 5,679,400 A | 10/1997 | Tuch |
| 5,693,085 A | 12/1997 | Buirge et al. |
| 5,697,967 A | 12/1997 | Dinh et al. |
| 5,697,971 A | 12/1997 | Fischell et al. |
| 5,700,286 A | 12/1997 | Tartaglia et al. |
| 5,707,385 A | 1/1998 | Williams |
| 5,713,949 A | 2/1998 | Jayaranman |
| 5,716,981 A | 2/1998 | Hunter et al. |
| 5,722,979 A | 3/1998 | Kusleika |
| 5,725,548 A | 3/1998 | Jayaraman |
| 5,725,549 A | 3/1998 | Lam |
| 5,725,567 A | 3/1998 | Wolff et al. |
| 5,728,150 A | 3/1998 | McDonald et al. |
| 5,728,420 A | 3/1998 | Keogh |
| 5,733,327 A | 3/1998 | Igaki et al. |
| 5,733,330 A | 3/1998 | Cox |
| 5,733,925 A | 3/1998 | Kunz et al. |
| 5,735,897 A | 4/1998 | Buirge |
| 5,741,293 A | 4/1998 | Wijay |
| 5,744,460 A | 4/1998 | Muller et al. |
| 5,755,772 A | 5/1998 | Evans et al. |
| 5,759,192 A | 6/1998 | Saunders |
| 5,766,239 A | 6/1998 | Cox |
| 5,769,883 A | 6/1998 | Buscemi et al. |
| 5,770,609 A | 6/1998 | Grainger et al. |
| 5,773,479 A | 6/1998 | Grainger et al. |
| 5,776,162 A | 7/1998 | Kleshinski |
| 5,776,181 A | 7/1998 | Lee et al. |
| 5,776,184 A | 7/1998 | Tuch |

| Patent | Date | Inventor |
|---|---|---|
| 5,782,908 A | 7/1998 | Cahalan et al. |
| 5,788,979 A | 8/1998 | Alt et al. |
| 5,792,106 A | 8/1998 | Mische |
| 5,797,898 A | 8/1998 | Santini et al. |
| 5,799,384 A | 9/1998 | Schwartz et al. |
| 5,800,507 A | 9/1998 | Schwartz |
| 5,807,404 A | 9/1998 | Richter |
| 5,811,447 A | 9/1998 | Kunz et al. |
| 5,817,152 A | 10/1998 | Birdsall et al. |
| 5,820,917 A | 10/1998 | Tuch |
| 5,820,918 A | 10/1998 | Ronan et al. |
| 5,824,045 A | 10/1998 | Alt |
| 5,824,048 A | 10/1998 | Tuch |
| 5,824,049 A | 10/1998 | Ragheb et al. |
| 5,827,322 A | 10/1998 | Williams |
| 5,833,651 A | 11/1998 | Donovan et al. |
| 5,837,008 A | 11/1998 | Berg et al. |
| 5,837,313 A | 11/1998 | Ding et al. |
| 5,843,117 A | 12/1998 | Alt et al. |
| 5,843,120 A | 12/1998 | Israel et al. |
| 5,843,166 A | 12/1998 | Lentz et al. |
| 5,843,172 A | 12/1998 | Yan |
| 5,843,175 A | 12/1998 | Frantzen |
| 5,843,741 A | 12/1998 | Wong et al. |
| 5,849,034 A | 12/1998 | Schwartz |
| 5,851,217 A | 12/1998 | Wolff et al. |
| 5,851,231 A | 12/1998 | Wolff et al. |
| 5,853,419 A | 12/1998 | Imran |
| 5,855,600 A | 1/1999 | Alt |
| 5,865,814 A | 2/1999 | Tuch |
| 5,868,781 A | 2/1999 | Killion |
| 5,871,535 A | 2/1999 | Wolff et al. |
| 5,873,904 A | 2/1999 | Ragheb et al. |
| 5,876,419 A | 3/1999 | Carpenter et al. |
| 5,879,697 A | 3/1999 | Ding et al. |
| 5,882,335 A | 3/1999 | Leone et al. |
| 5,886,026 A | 3/1999 | Hunter et al. |
| 5,891,108 A | 4/1999 | Leone et al. |
| 5,893,840 A | 4/1999 | Hull et al. |
| 5,922,020 A | 7/1999 | Klein et al. |
| 5,922,021 A | 7/1999 | Jang |
| 5,928,916 A | 7/1999 | Keogh |
| 5,932,243 A | 8/1999 | Fricker et al. |
| 5,935,506 A | 8/1999 | Schmitz et al. |
| 5,945,456 A | 8/1999 | Grainger et al. |
| 5,957,971 A | 9/1999 | Schwartz |
| 5,964,798 A | 10/1999 | Imran |
| 5,968,091 A | 10/1999 | Pinchuk et al. |
| 5,968,092 A | 10/1999 | Buscemi et al. |
| 5,972,027 A | 10/1999 | Johnson |
| 5,976,182 A | 11/1999 | Cox |
| 5,980,551 A | 11/1999 | Summers et al. |
| 5,980,972 A | 11/1999 | Ding |
| 5,981,568 A | 11/1999 | Kunz et al. |
| 5,984,957 A | 11/1999 | Laptewicz, Jr. et al. |
| 5,992,769 A | 11/1999 | Wise |
| 5,994,341 A | 11/1999 | Hunter et al. |
| 6,007,517 A | 12/1999 | Anderson |
| 6,015,432 A | 1/2000 | Rakos et al. |
| 6,017,362 A | 1/2000 | Lau |
| 6,017,363 A | 1/2000 | Hojeibane |
| 6,019,789 A | 2/2000 | Dinh et al. |
| 6,022,371 A | 2/2000 | Killion |
| 6,024,740 A | 2/2000 | Lesh et al. |
| 6,027,526 A | 2/2000 | Limon et al. |
| 6,030,414 A | 2/2000 | Taheri |
| 6,042,606 A | 3/2000 | Frantzen |
| 6,056,722 A | 5/2000 | Jayaraman |
| 6,063,101 A | 5/2000 | Jacobsen et al. |
| 6,071,305 A | 6/2000 | Brown et al. |
| 6,074,659 A | 6/2000 | Kunz et al. |
| 6,083,258 A | 7/2000 | Yadav |
| 6,086,582 A | 7/2000 | Altman et al. |
| 6,087,479 A | 7/2000 | Stamler et al. |
| 6,096,070 A | 8/2000 | Ragheb et al. |
| 6,099,561 A | 8/2000 | Alt |
| 6,099,562 A | 8/2000 | Ding et al. |
| 6,117,101 A | 9/2000 | Diederich et al. |
| 6,120,535 A | 9/2000 | McDonald et al. |
| 6,120,536 A | 9/2000 | Ding et al. |
| 6,120,847 A | 9/2000 | Yang et al. |
| 6,121,027 A | 9/2000 | Clapper et al. |
| 6,123,861 A | 9/2000 | Santini et al. |
| 6,140,127 A | 10/2000 | Sprague |
| 6,153,252 A | 11/2000 | Hossainy et al. |
| 6,156,062 A | 12/2000 | McGuinness |
| 6,159,488 A | 12/2000 | Nagler et al. |
| 6,171,609 B1 | 1/2001 | Kunz |
| 6,174,325 B1 | 1/2001 | Eckhouse |
| 6,193,746 B1 | 2/2001 | Strecker |
| 6,203,569 B1 | 3/2001 | Wijay |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,239,118 B1 | 5/2001 | Schatz et al. |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,254,632 B1 | 7/2001 | Wu et al. |
| 6,261,318 B1 | 7/2001 | Lee et al. |
| 6,268,390 B1 | 7/2001 | Kunz |
| 6,273,908 B1 | 8/2001 | Ndondo-Lay |
| 6,273,910 B1 | 8/2001 | Limon |
| 6,273,911 B1 | 8/2001 | Cox et al. |
| 6,273,913 B1 | 8/2001 | Wright et al. |
| 6,280,411 B1 | 8/2001 | Lennox |
| 6,287,332 B1 | 9/2001 | Bolz et al. |
| 6,290,673 B1 | 9/2001 | Shanley |
| 6,293,967 B1 | 9/2001 | Shanley |
| 6,299,604 B1 | 10/2001 | Ragheb et al. |
| 6,306,166 B1 | 10/2001 | Barry et al. |
| 6,306,421 B1 | 10/2001 | Kunz et al. |
| 6,309,414 B1 | 10/2001 | Rolando et al. |
| 6,312,459 B1 | 11/2001 | Huang et al. |
| 6,312,460 B2 | 11/2001 | Drasler et al. |
| 6,331,189 B1 | 12/2001 | Wolinsky et al. |
| 6,334,871 B1 | 1/2002 | Dor et al. |
| 6,338,739 B1 | 1/2002 | Datta et al. |
| 6,358,556 B1 | 3/2002 | Ding et al. |
| 6,358,989 B1 | 3/2002 | Kunz et al. |
| 6,368,346 B1 | 4/2002 | Jadhav |
| 6,369,039 B1 | 4/2002 | Palasis et al. |
| 6,379,381 B1 | 4/2002 | Hossainy et al. |
| 6,387,124 B1 | 5/2002 | Buscemi et al. |
| 6,395,326 B1 * | 5/2002 | Castro et al. ................. 427/2.24 |
| 6,399,144 B2 | 6/2002 | Dinh et al. |
| 6,403,635 B1 | 6/2002 | Kinsella et al. |
| 6,423,092 B2 | 7/2002 | Datta et al. |
| 6,423,345 B2 | 7/2002 | Bernstein et al. |
| 6,429,232 B1 | 8/2002 | Kinsella et al. |
| 6,451,051 B2 | 9/2002 | Drasler et al. |
| 6,461,631 B1 | 10/2002 | Dunn et al. |
| 6,468,302 B2 | 10/2002 | Cox et al. |
| 6,475,237 B2 | 11/2002 | Drasler et al. |
| 6,482,810 B1 | 11/2002 | Brem et al. |
| 6,491,617 B1 | 12/2002 | Ogle et al. |
| 6,491,666 B1 | 12/2002 | Santini et al. |
| 6,491,938 B2 | 12/2002 | Kunz et al. |
| 6,497,916 B1 | 12/2002 | Taylor et al. |
| 6,500,859 B2 | 12/2002 | Kinsella et al. |
| 6,503,954 B1 | 1/2003 | Bhat et al. |
| 6,506,411 B2 | 1/2003 | Hunter et al. |
| 6,506,437 B1 | 1/2003 | Harish et al. |
| 6,511,505 B2 | 1/2003 | Cox et al. |
| 6,515,009 B1 | 2/2003 | Kunz et al. |
| 6,527,799 B2 | 3/2003 | Shanley |
| 6,528,121 B2 | 3/2003 | Ona et al. |
| 6,530,950 B1 | 3/2003 | Alvarado et al. |
| 6,530,951 B1 | 3/2003 | Bates et al. |
| 6,533,807 B2 | 3/2003 | Wolinsky et al. |
| 6,537,256 B2 | 3/2003 | Santini et al. |
| 6,540,774 B1 | 4/2003 | Cox |
| 6,544,544 B2 | 4/2003 | Hunter et al. |
| 6,551,303 B1 | 4/2003 | Van Tassel et al. |
| 6,551,838 B2 | 4/2003 | Santini et al. |
| 6,558,733 B1 | 5/2003 | Hossainy et al. |

| | | | | | | |
|---|---|---|---|---|---|---|
| 6,562,065 B1 | 5/2003 | Shanley | | 2002/0007209 A1 | 1/2002 | De Scheerder et al. |
| 6,565,602 B2 | 5/2003 | Rolando et al. | | 2002/0007213 A1 | 1/2002 | Falotico et al. |
| 6,569,441 B2 | 5/2003 | Kunz et al. | | 2002/0007214 A1 | 1/2002 | Falotico |
| 6,569,688 B2 | 5/2003 | Sivan et al. | | 2002/0007215 A1 | 1/2002 | Falotico et al. |
| 6,572,642 B2 | 6/2003 | Rinaldi et al. | | 2002/0010507 A1 | 1/2002 | De Scheerder et al. |
| 6,585,764 B2 | 7/2003 | Wright et al. | | 2002/0013619 A1 | 1/2002 | Shanley |
| 6,585,765 B1 | 7/2003 | Hossainy et al. | | 2002/0016625 A1 | 2/2002 | Falotico et al. |
| 6,585,773 B1 | 7/2003 | Xie | | 2002/0019661 A1 | 2/2002 | Datta et al. |
| 6,599,314 B2 | 7/2003 | Mathis | | 2002/0022876 A1 | 2/2002 | Richter et al. |
| 6,599,928 B2 | 7/2003 | Kunz et al. | | 2002/0028243 A1 | 3/2002 | Bates et al. |
| 6,602,284 B2 | 8/2003 | Cox et al. | | 2002/0032414 A1 | 3/2002 | Ragheb et al. |
| 6,613,084 B2 | 9/2003 | Yang | | 2002/0038145 A1 | 3/2002 | Jang |
| 6,616,690 B2 | 9/2003 | Rolando et al. | | 2002/0038146 A1 | 3/2002 | Ulf |
| 6,627,246 B2 | 9/2003 | Mehta et al. | | 2002/0041931 A1 | 4/2002 | Suntola et al. |
| 6,635,082 B1 | 10/2003 | Hossainy et al. | | 2002/0068969 A1 | 6/2002 | Shanley et al. |
| 6,638,302 B1 | 10/2003 | Curcio et al. | | 2002/0071902 A1 | 6/2002 | Ding et al. |
| 6,645,547 B1 | 11/2003 | Shekalim et al. | | 2002/0072511 A1 | 6/2002 | New et al. |
| 6,656,162 B2 * | 12/2003 | Santini et al. ............. 604/191 | | 2002/0082679 A1 | 6/2002 | Sirhan et al. |
| 6,656,217 B1 | 12/2003 | Herzog, Jr. et al. | | 2002/0082680 A1 | 6/2002 | Shanley et al. |
| 6,663,664 B1 | 12/2003 | Pacetti | | 2002/0082682 A1 | 6/2002 | Barclay et al. |
| 6,663,881 B2 | 12/2003 | Kunz et al. | | 2002/0094985 A1 | 7/2002 | Herrmann et al. |
| 6,673,385 B1 | 1/2004 | Ding et al. | | 2002/0107563 A1 | 8/2002 | Shanley |
| 6,682,545 B1 | 1/2004 | Kester | | 2002/0123801 A1 | 9/2002 | Pacetti et al. |
| 6,689,390 B2 | 2/2004 | Bernstein et al. | | 2002/0127263 A1 | 9/2002 | Carlyle et al. |
| 6,699,281 B2 | 3/2004 | Vallana et al. | | 2002/0128704 A1 | 9/2002 | Daum et al. |
| 6,702,850 B1 | 3/2004 | Byun et al. | | 2002/0142039 A1 | 10/2002 | Claude |
| 6,706,061 B1 | 3/2004 | Fischell et al. | | 2002/0155212 A1 | 10/2002 | Hossainy |
| 6,712,845 B2 | 3/2004 | Hossainy | | 2002/0165604 A1 | 11/2002 | Shanley |
| 6,713,119 B2 | 3/2004 | Hossainy et al. | | 2002/0193475 A1 | 12/2002 | Hossainy et al. |
| 6,716,242 B1 | 4/2004 | Altman | | 2003/0004141 A1 | 1/2003 | Brown |
| 6,716,444 B1 | 4/2004 | Castro et al. | | 2003/0004564 A1 | 1/2003 | Elkins et al. |
| 6,716,981 B2 | 4/2004 | Hunter et al. | | 2003/0009214 A1 | 1/2003 | Shanley |
| 6,720,350 B2 | 4/2004 | Kunz et al. | | 2003/0018083 A1 | 1/2003 | Jerussi et al. |
| 6,723,373 B1 | 4/2004 | Narayanan et al. | | 2003/0028244 A1 | 2/2003 | Bates et al. |
| 6,730,064 B2 | 5/2004 | Ragheb et al. | | 2003/0036794 A1 | 2/2003 | Ragheb et al. |
| 6,730,116 B1 | 5/2004 | Wolinsky et al. | | 2003/0050687 A1 | 3/2003 | Schwade et al. |
| 6,746,773 B2 | 6/2004 | Llanos et al. | | 2003/0060877 A1 | 3/2003 | Falotico et al. |
| 6,752,829 B2 | 6/2004 | Kocur et al. | | 2003/0068355 A1 | 4/2003 | Shanley et al. |
| 6,753,071 B1 | 6/2004 | Pacetti | | 2003/0069606 A1 | 4/2003 | Girouard et al. |
| 6,758,859 B1 | 7/2004 | Dang et al. | | 2003/0077312 A1 | 4/2003 | Schmulewicz et al. |
| 6,764,507 B2 | 7/2004 | Shanley et al. | | 2003/0083646 A1 | 5/2003 | Sirhan et al. |
| 6,776,796 B2 | 8/2004 | Falotico et al. | | 2003/0086957 A1 | 5/2003 | Hughes et al. |
| 6,780,424 B2 | 8/2004 | Claude | | 2003/0088307 A1 | 5/2003 | Shulze et al. |
| 6,783,543 B2 | 8/2004 | Jang | | 2003/0100865 A1 | 5/2003 | Santini et al. |
| 6,783,793 B1 | 8/2004 | Hossainy et al. | | 2003/0105511 A1 | 6/2003 | Welsh et al. |
| 6,790,228 B2 | 9/2004 | Hossainy et al. | | 2003/0125803 A1 | 7/2003 | Vallana et al. |
| 6,805,898 B1 | 10/2004 | Wu et al. | | 2003/0157241 A1 | 8/2003 | Hossainy et al. |
| 6,808,536 B2 | 10/2004 | Wright et al. | | 2003/0167085 A1 | 9/2003 | Shanley |
| 6,818,063 B1 | 11/2004 | Kerrigan | | 2003/0176915 A1 | 9/2003 | Wright et al. |
| 6,846,841 B2 | 1/2005 | Hunter et al. | | 2003/0181973 A1 | 9/2003 | Sahota |
| 6,849,089 B2 | 2/2005 | Stoll | | 2003/0199970 A1 | 10/2003 | Shanley |
| 6,852,123 B2 | 2/2005 | Brown | | 2003/0204239 A1 | 10/2003 | Carlyle et al. |
| 6,855,125 B2 | 2/2005 | Shanley | | 2003/0216699 A1 | 11/2003 | Falotico |
| 6,855,770 B2 | 2/2005 | Pinchuk et al. | | 2003/0225420 A1 | 12/2003 | Wardle |
| 6,860,946 B2 | 3/2005 | Hossainy et al. | | 2004/0006382 A1 | 1/2004 | Sohier |
| 6,861,088 B2 | 3/2005 | Weber et al. | | 2004/0010306 A1 | 1/2004 | Freyman et al. |
| 6,863,685 B2 | 3/2005 | Davila et al. | | 2004/0024449 A1 | 2/2004 | Boyle |
| 6,869,443 B2 | 3/2005 | Buscemi et al. | | 2004/0073296 A1 | 4/2004 | Epstein et al. |
| 6,887,510 B2 | 5/2005 | Villareal | | 2004/0122505 A1 | 6/2004 | Shanley |
| 6,890,339 B2 | 5/2005 | Sahatjian et al. | | 2004/0122506 A1 | 6/2004 | Shanley et al. |
| 6,896,965 B1 | 5/2005 | Hossainy | | 2004/0127976 A1 | 7/2004 | Diaz |
| 6,908,622 B2 | 6/2005 | Barry et al. | | 2004/0127977 A1 | 7/2004 | Shanley |
| 6,908,624 B2 | 6/2005 | Hossainy et al. | | 2004/0142014 A1 | 7/2004 | Litvack et al. |
| 6,929,660 B1 | 8/2005 | Ainsworth et al. | | 2004/0143321 A1 | 7/2004 | Litvack et al. |
| 6,939,376 B2 | 9/2005 | Shulze et al. | | 2004/0143322 A1 | 7/2004 | Litvack et al. |
| 6,964,680 B2 | 11/2005 | Shanley | | 2004/0166140 A1 | 8/2004 | Santini et al. |
| 7,056,338 B2 | 6/2006 | Shanley et al. | | 2004/0193255 A1 | 9/2004 | Shanley et al. |
| 7,192,438 B2 | 3/2007 | Margolis | | 2004/0202692 A1 | 10/2004 | Shanley et al. |
| 7,195,628 B2 | 3/2007 | Falkenberg | | 2004/0204756 A1 | 10/2004 | Diaz et al. |
| 7,429,268 B2 | 9/2008 | Shanley et al. | | 2004/0220660 A1 | 11/2004 | Shanley et al. |
| 2001/0000802 A1 | 5/2001 | Soykan et al. | | 2004/0220665 A1 | 11/2004 | Hossainy et al. |
| 2001/0018469 A1 | 8/2001 | Chen et al. | | 2004/0225350 A1 | 11/2004 | Shanley |
| 2001/0027340 A1 | 10/2001 | Wright et al. | | 2004/0249449 A1 | 12/2004 | Shanley et al. |
| 2001/0029351 A1 | 10/2001 | Falotico et al. | | 2005/0058684 A1 | 3/2005 | Shanley et al. |
| 2001/0034363 A1 | 10/2001 | Li et al. | | 2005/0059991 A1 | 3/2005 | Shanley |
| 2001/0044648 A1 | 11/2001 | Wolinsky et al. | | 2005/0060020 A1 | 3/2005 | Jenson |
| 2001/0044652 A1 | 11/2001 | Moore | | 2005/0074545 A1 | 4/2005 | Thoman |
| 2002/0002400 A1 | 1/2002 | Drasler et al. | | 2005/0075714 A1 | 4/2005 | Cheng et al. |
| 2002/0005206 A1 | 1/2002 | Falotico et al. | | 2005/0100577 A1 | 5/2005 | Parker et al. |

| | | | | | | |
|---|---|---|---|---|---|---|
| 2005/0119720 | A1 | 6/2005 | Gale et al. | EP | 1348402 A1 | 10/2003 |
| 2005/0137678 | A1 | 6/2005 | Varma | EP | 1498084 | 1/2005 |
| 2005/0222676 | A1 | 10/2005 | Shanley et al. | EP | 1181903 | 2/2005 |
| 2005/0234538 | A1 | 10/2005 | Litvack et al. | EP | 1527754 | 5/2005 |
| 2005/0234544 | A1 | 10/2005 | Shanley | EP | 1561436 | 8/2005 |
| 2005/0278016 | A1 | 12/2005 | Welsh et al. | EP | 1570807 A2 | 9/2005 |
| 2006/0008503 | A1 | 1/2006 | Shanley | EP | 968013 | 10/2005 |
| 2006/0009838 | A1 | 1/2006 | Shanley et al. | EP | 1582180 | 10/2005 |
| 2006/0096660 | A1 | 5/2006 | Diaz | EP | 1600180 | 11/2005 |
| 2006/0122688 | A1 | 6/2006 | Shanley et al. | EP | 1 772 114 A1 | 4/2007 |
| 2006/0122697 | A1 | 6/2006 | Shanley et al. | FR | 2 683 449 | 5/1993 |
| 2007/0067026 | A1 | 3/2007 | Shanley | FR | 2 764 794 A1 | 12/1998 |
| 2008/0097579 | A1 | 4/2008 | Shanley et al. | WO | 90/01969 A1 | 3/1990 |
| 2008/0097583 | A1 | 4/2008 | Shanley et al. | WO | 90/13332 A1 | 11/1990 |
| 2008/0109071 | A1 | 5/2008 | Shanley | WO | 91/10424 A1 | 7/1991 |
| 2008/0243070 | A1 | 10/2008 | Shanley | WO | 91/11193 A1 | 8/1991 |
| 2008/0249609 | A1 | 10/2008 | Shanley | WO | 91/12779 A1 | 9/1991 |
| | | | | WO | 91/17789 A1 | 11/1991 |

FOREIGN PATENT DOCUMENTS

| | | | | | |
|---|---|---|---|---|---|
| | | | WO | 92/00747 A1 | 1/1992 |
| | | | WO | 92/12717 A2 | 8/1992 |
| CA | 2323358 C | 10/1999 | WO | 92/15286 A1 | 9/1992 |
| CA | 2409787 A1 | 12/2001 | WO | 93/06792 A1 | 4/1993 |
| DE | 20200220 | 4/2002 | WO | 93/11120 A1 | 6/1993 |
| DE | 20200220 U1 | 4/2002 | WO | 94/07529 A1 | 4/1994 |
| EP | 0 294 905 B1 | 12/1988 | WO | 94/13268 A1 | 6/1994 |
| EP | 0294905 B1 | 12/1988 | WO | 94/21308 A1 | 9/1994 |
| EP | 0 335 341 B1 | 10/1989 | WO | 94/24961 A1 | 11/1994 |
| EP | 0374698 A2 | 6/1990 | WO | 94/24962 A1 | 11/1994 |
| EP | 0 470 569 B1 | 2/1992 | WO | 95/03036 A1 | 2/1995 |
| EP | 0470246 B1 | 2/1992 | WO | 95/03795 A1 | 2/1995 |
| EP | 0 540 290 B1 | 5/1993 | WO | 95/03796 A1 | 2/1995 |
| EP | 0543653 A1 | 5/1993 | WO | 95/24908 A1 | 9/1995 |
| EP | 0551182 B1 | 7/1993 | WO | 95/25176 A1 | 9/1995 |
| EP | 0 556 245 B1 | 8/1993 | WO | 95/34255 A1 | 12/1995 |
| EP | 0 566 245 B1 | 10/1993 | WO | 96/03092 A1 | 2/1996 |
| EP | 0566245 B1 | 10/1993 | WO | 96/29028 A1 | 9/1996 |
| EP | 0566807 B1 | 10/1993 | WO | 96/32907 A1 | 10/1996 |
| EP | 0 567 816 B1 | 11/1993 | WO | 97/04721 A1 | 2/1997 |
| EP | 0568310 B1 | 11/1993 | WO | 97/10011 A1 | 3/1997 |
| EP | 0604022 A1 | 6/1994 | WO | 97/33534 A1 | 9/1997 |
| EP | 0623354 B1 | 11/1994 | WO | 97/40783 A2 | 11/1997 |
| EP | 0627226 B1 | 12/1994 | WO | 98/00107 A2 | 1/1998 |
| EP | 0679373 B1 | 11/1995 | WO | 98/05270 A1 | 2/1998 |
| EP | 0706376 B1 | 4/1996 | WO | 98/06092 A1 | 2/1998 |
| EP | 0711158 B1 | 5/1996 | WO | 98/08566 A1 | 3/1998 |
| EP | 0712615 B1 | 5/1996 | WO | 98/18407 A1 | 5/1998 |
| EP | 0716836 B1 | 6/1996 | WO | 98/19628 A1 | 5/1998 |
| EP | 0 734 698 B1 | 10/1996 | WO | 98/23228 A1 | 6/1998 |
| EP | 747069 | 12/1996 | WO | 98/23244 A1 | 6/1998 |
| EP | 0752885 B1 | 1/1997 | WO | WO-9823228 | 6/1998 |
| EP | 0761251 B1 | 3/1997 | WO | 98/34669 A1 | 8/1998 |
| EP | 0 706 376 B1 | 4/1997 | WO | 98/36784 A1 | 8/1998 |
| EP | 0770401 B1 | 5/1997 | WO | WO-9836784 | 8/1998 |
| EP | 0797963 A2 | 10/1997 | WO | 98/47447 A1 | 10/1998 |
| EP | 0809515 B1 | 12/1997 | WO | 98/56312 A1 | 12/1998 |
| EP | 0 824 902 B1 | 2/1998 | WO | 98/58600 A1 | 12/1998 |
| EP | 0832655 B1 | 4/1998 | WO | 99/15108 A2 | 4/1999 |
| EP | 0 850 604 B1 | 7/1998 | WO | 99/16386 A1 | 4/1999 |
| EP | 0 850 651 B1 | 7/1998 | WO | 99/16477 A2 | 4/1999 |
| EP | 0850651 B1 | 7/1998 | WO | WO-9916386 | 4/1999 |
| EP | 0 875 218 B1 | 11/1998 | WO | 99/36002 A1 | 7/1999 |
| EP | 875218 | 11/1998 | WO | 99/39661 A2 | 8/1999 |
| EP | 0 887 051 B1 | 12/1998 | WO | 99/44536 A1 | 9/1999 |
| EP | 0 897 700 B1 | 2/1999 | WO | 99/49810 A1 | 10/1999 |
| EP | 0934036 B1 | 8/1999 | WO | 99/49928 A1 | 10/1999 |
| EP | 0938878 B1 | 9/1999 | WO | WO-9949928 | 10/1999 |
| EP | 950386 | 10/1999 | WO | 99/55395 A1 | 11/1999 |
| EP | 0959812 B1 | 12/1999 | WO | 99/55396 A1 | 11/1999 |
| EP | 0980280 B1 | 2/2000 | WO | 00/10613 A2 | 3/2000 |
| EP | 1118325 B1 | 7/2001 | WO | WO-0010622 | 3/2000 |
| EP | 1132058 | 9/2001 | WO | 00/21584 A1 | 4/2000 |
| EP | 1172074 | 1/2002 | WO | 00/27445 A1 | 5/2000 |
| EP | 1 181 943 A1 | 2/2002 | WO | 00/32255 A1 | 6/2000 |
| EP | 1189554 B1 | 3/2002 | WO | 00/40278 A1 | 7/2000 |
| EP | 1 223 305 B1 | 7/2002 | WO | 00/45744 A1 | 8/2000 |
| EP | 1222941 | 7/2002 | WO | 00/69368 A2 | 11/2000 |
| EP | 1 236 478 B1 | 9/2002 | WO | 00/71054 A1 | 11/2000 |
| EP | 1 277 449 B1 | 1/2003 | WO | WO-0117577 | 3/2001 |
| EP | 1277449 | 1/2003 | WO | 01/45763 A1 | 6/2001 |
| EP | 0375520 B1 | 4/2003 | | | |

| | | |
|---|---|---|
| WO | 01/45862 A1 | 6/2001 |
| WO | 01/49338 A1 | 7/2001 |
| WO | 01/52915 A1 | 7/2001 |
| WO | 01/87342 A2 | 11/2001 |
| WO | 01/87376 A1 | 11/2001 |
| WO | 01/93781 A2 | 12/2001 |
| WO | 02/17880 A2 | 3/2002 |
| WO | 02/26162 A2 | 4/2002 |
| WO | 02/26281 A1 | 4/2002 |
| WO | WO-0226281 | 4/2002 |
| WO | WO-0232347 | 4/2002 |
| WO | 02/41931 A2 | 5/2002 |
| WO | 02/060506 A1 | 8/2002 |
| WO | WO-0206506 | 8/2002 |
| WO | 02/087586 A1 | 11/2002 |
| WO | 03/007842 A2 | 1/2003 |
| WO | WO-03015664 | 2/2003 |
| WO | 03/018083 A2 | 3/2003 |
| WO | 03/047463 A1 | 6/2003 |
| WO | 03/057218 A1 | 7/2003 |
| WO | WO-03077730 | 9/2003 |
| WO | WO-04043510 | 5/2004 |
| WO | WO-04043511 | 5/2004 |
| WO | WO-04087015 | 10/2004 |
| WO | WO-04096176 | 11/2004 |
| WO | WO-05004945 | 1/2005 |
| WO | WO-05027794 | 3/2005 |
| WO | 2005/053937 A1 | 6/2005 |
| WO | 2005/118971 A2 | 12/2005 |
| WO | WO-05115277 | 12/2005 |
| WO | WO-05120397 | 12/2005 |
| WO | 2006/036319 A2 | 4/2006 |

OTHER PUBLICATIONS

Berk, Bradford C. MD et al., Pharmacologic Roles of Heparin and Glucocorticoids to Prevent Restenosis After Coronary Angioplasty, Jacc, vol. 17, No. 6, May 1991: 111B-7B.

Campbell, Gordon R. et al., Phenotypic Modulation of Smooth Muscle Cells in Primary Culture, Vascular Smooth Muscle Cells in Culture, CRC Press 1987, pp. 39-55.

Clowes, Alexander W. et al., Significance of Quiescent Smooth Muscle Migration in the Injured Rat Carotid Artery, Cir Res 56: 139-145, 1985.

Clowes, Alexander W. et al., Suppression by Heparin of smooth muscle cell proliferation in injured arteries, Nature, vol. 265, Feb. 17, 1977, 625-626.

Clowes, Alexander W. et al., Kinetics of Cellular Proliferation after Arterial Injury, Circulation Research, vol. 58, No. 6, Jun. 1986, 839-845.

Coburn, Michael D., MD et al., Dose Responsive Suppression of Myointimal Hyperlasia by Dexamethasone, Journal of Vascular Surgery, vol. 15, No. 3, Mar. 1992, 510-518.

Fischman, David L., MD et al., A Randomized Comparison of coronary-Stent Implantation with Balloon Angioplasty in Treatment of Coronary Artery Disease, The New England Journal of Medicine, vol. 331, No. 8, Aug. 25, 1994, 496-501.

Franklin, Stephen, M. MD et al., Pharmacologic prevention of restenosis after coronary angioplasty: review of the randomized clinical trials, Coronary Artery Disease, Mar. 1993, vol. 4, No. 3, 232-242.

Grayson, A.C. Richards et al., "Multi-pulse Drug Delivery From a Resorbable Polymeric Microchip Device", Nature Materials, vol. 2, Nov. 2003, pp. 767-770.

Gregory, Clare R. et al., Rapamycin Inhibits Arterial Intimal Thickening Caused by Both Alloimmune and Mechanical Injury, Transplantation vol. 55, No. 6, Jun. 1993, 1409-1418.

Guyton, John, R. et al., Inhibition of Rat Arterial Smooth Muscle Cell Proliferation by Heparin, Circulation Research, vol. 46, No. 5, May 1980, 625-634.

Hakan, E. et al., The Jostent Coronary Stent Range, Ch. 19.

Halsey, W. (ed.): Dictionary A-K, New York: Macmillan Educational Co., 1986, pp. 491.

Hasson, Goran K., MD., et al., Interferon—Inhibits Arterial Stenosis After Injury, Circulation, vol. 84, No. 3, Sep. 1991, 1266-1272.

Hiatt, B.L. et al., "The Drug-Eluting Stent: Is it the Holy Grail?" Reviews in Cardiovascular medicine, 2001, vol. 2, No. 4, pp. 190-196.

Hwang, C>W> et al., Physiological Transport Forces Govern Drug Distribution for Stent-based Delivery, Circulation, 104, 2001, pp. 600-605.

Kornowski, R. et al., "Slow-Release Taxol coated GR11 Stents Reduce Neointima Formation in a Porcine Coronary in Stent Restenosis Model" Abstract from the American Hear Associatiion's 70th Scientific Sessions, Nov. 9-12, 1997.

Jonasson, Lena et al, Cyclosporin A inhibits smooth muscle proliferation in the vascular response to injury, Proc. Natl. Acad. Sci USA 85 (1988), pp. 2303-2306.

Lange, Richard A. MD et al., Restenosis After Coronary Balloon Angioplasty, Annu. Rev. Med. 1991, 42:127-32.

Liu, Ming Wei, MD et al., Restenosis After Coronary Angioplasty Potential Biologic Determinants and Role of Intimal Hyperplasia, Circulation 1989, 79:1374-1387.

Liu, Ming, W. MD et al., Trapidil in Preventing Restenosis After Balloon Angioplasty in the Atherosclerotic Rabbit, Circulation, vol. 81, No. 3, Mar. 1990, 1089-1093.

Lundergan, Conor F., MD et al., Peptide Inhibition of Myointimal Proliferation by Angiopeptin, a Somatostation Analogue, Jacc, vol. 17, No. 6, May 1991: 132B-6B.

Majesky, Mark W., et al., Heparin Regulates Smooth Muscle S Phase Entry in the Injured Rat Carotid Artery, Circulation Research, vol. 61, No. 2, Aug. 1987, 296-300.

Marx, Steven O. et al., Rapamycin-FKBP Inhibits Cell Cycle Regulators of Proliferation in Vascular Smooth Muscle Cells, Circulation Research, 1995; 76(3):412-417.

Nemecek, Georgina M. et al., Terbinafine Inhibits the Mitogenic Response to Platelet-Derived Growth Factor in Vitro and Neointimal Proliferation in Vivo, The Journal of Pharmacology and Experimental Therapeutics, vol. 248, No. 3, 1998, 1167-1174.

Okada, Tomohisa, MD et al., Localized Release of Perivascular Heparin Inhibits Intimal Proliferaiton after Endothelial Injury without Systemic Anticoagulation, Neurosurgery, vol. 25, No. 6,1989, 892-898.

Poon, Michael et al., Rapamycin Inhibits Vascular Smooth Muscle Cell Migration, J. Clin. Invest., vol. 98, No. 10, Nov. 1996, 2277-2283.

Popma, Jeffrey J. MD et al., Clinical Trials of Restenosis After Coronary Angioplasty, Circulation vol. 84, No. 3, Sep. 1991, 1426-1436.

Powell, Jerry S. et al., Inhibitors of Angiotensin-Converting Enzyme Prevent Myointimal Proliferation After Vascular Injury, Science, vol. 245, Jul. 14, 1989, 186-188.

Reifart, Nicolaus et al., The JOSTENT Coronary Stent Range, JOMED International AB, Heisingborg, Sweden, Chapter 16, pp. 123-140.

Siekierka, John J., Probing T-Cell Signal Transduction Pathways with the Immunosuppressive Drugs, FK-506 and Rapamycin, Immunologic Research 1994,13:110-116.

Snow, Alan D. et al., Heparin Modulates the Composition of th Extracellular Matrix Domain Surrounding Arterial Smooth Muscle Cells, American Journal of Pathology, vol. 137, No. 2, Aug. 1990, 313-330.

Serruys, P. W. et al., Evaluation of Ketanserin in the Prevention of Restenosis After Percutaneous Transluminal Coronary Angioplasty—A Multicenter Randomized Double-Blind Placebo-Controlled Trial, Circulation, vol. 88, No. 4, Part 1, Oct. 1993, 1588-1601.

Serruys, Patrick W. et al., Heparin-Coated Palmaz-Schatz Stents in Human Coronary Arteries, Circulation, 1996, 93:412-422.

Vasey, Charles G. et al., Clinical Cardiology: Stress Echo and Coronary Flow, Supplement II Circulation, vol. 80, No. 4, Oct. 1989,11-66.

* cited by examiner

EXPANDABLE MEDICAL DEVICE FOR DELIVERY OF BENEFICIAL AGENT

CROSS-REFERENCE TO RELATED APPLICATIONS

This application is a continuation of pending U.S. application Ser. No. 10/729,631, filed Dec. 5, 2003, which is a continuation of pending U.S. application Ser. No. 09/948,989, filed Sep. 7, 2001, which claims priority under 35 U.S.C. §119(e) to U.S. Provisional Application Ser. No. 60/314,259, filed Aug. 20, 2001, which is incorporated herein by reference in its entirety.

BACKGROUND OF THE INVENTION

1. Field of the Invention

The present invention relates to tissue-supporting medical devices, and more particularly to expandable, non-removable devices that are implanted within a bodily lumen of a living animal or human to support the organ and maintain patency, and that can deliver a beneficial agent to the intervention site.

2. Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as, stainless steel, gold, silver, tantalum, titanium, and shape memory alloys such as Nitinol.

U.S. Pat. Nos. 4,733,665; 4,739,762; and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body. U.S. Pat. No. 5,545,210 discloses a thin-walled tubular stent geometrically similar to those discussed above, but constructed of a nickel-titanium shape memory alloy ("Nitinol"), which can be permanently fixed within the body without exceeding its elastic limit. All of these stents share a critical design property: in each design, the features that undergo permanent deformation during stent expansion are prismatic, i.e., the cross sections of these features remain constant or change very gradually along their entire active length. These prismatic structures are ideally suited to providing large amounts of elastic deformation before permanent deformation commences, which in turn leads to sub-optimal device performance in important properties including stent expansion force, stent recoil, strut element stability, stent securement on delivery catheters, and radiopacity.

U.S. Pat. No. 6,241,762, which is incorporated herein by reference in its entirety, discloses a non-prismatic stent design which remedies the above mentioned performance deficiencies of previous stents. In addition, preferred embodiments of this patent provide a stent with large, non-deforming strut and link elements, which can contain holes without compromising the mechanical properties of the strut or link elements, or the device as a whole. Further, these holes may serve as large, protected reservoirs for delivering various beneficial agents to the device implantation site.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition and vascular smooth muscle cell proliferation, and which may ultimately result in renarrowing or even reocclusion of the lumen. Despite the introduction of improved surgical techniques, devices and pharmaceutical agents, the overall restenosis rate is still reported in the range of 25% to 50% within six to twelve months after an angioplasty procedure. To treat this condition, additional revascularization procedures are frequently required, thereby increasing trauma and risk to the patient.

Some of the techniques under development to address the problem of restenosis include irradiation of the injury site and the use of conventional stents to deliver a variety of beneficial or pharmaceutical agents to the wall of the traumatized vessel. In the latter case, a conventional stent is frequently surface-coated with a beneficial agent (often a drug-impregnated polymer) and implanted at the angioplasty site. Alternatively, an external drug-impregnated polymer sheath is mounted over the stent and co-deployed in the vessel.

While acute outcomes from radiation therapies appeared promising initially, long term beneficial outcomes have been limited to reduction in restenosis occurring within a previously implanted stent, so-called 'in-stent' restenosis. Radiation therapies have not been effective for preventing restenosis in de novo lesions. Polymer sheaths that span stent struts have also proven problematic in human clinical trials due to the danger of blocking flow to branch arteries, incomplete apposition of stent struts to arterial walls and other problems. Unacceptably high levels of MACE (Major Adverse Cardiac Events that include death, heart attack, or the need for a repeat angioplasty or coronary artery bypass surgery) have resulted in early termination of clinical trials for sheath covered stents.

Conventional stents with surface coatings of various beneficial agents, by contrast, have shown promising early results. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, durations, and the like that can be achieved.

In addition to sub-optimal release profiles, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded, which permits differential motion between the stent and adjacent tissue. Resulting problems include microabrasion and inflammation, stent drift, and failure to re-endothelialize the vessel wall.

Another significant problem is that expansion of the stent may stress the overlying polymeric coating causing the coating to plastically deform or even to rupture, which may therefore effect drug release kinetics or have other untoward effects. Further, expansion of such a coated stent in an atherosclerotic blood vessel will place circumferential shear forces on the polymeric coating, which may cause the coating to separate from the underlying stent surface. Such separation may again have untoward effects including embolization of coating fragments causing vascular obstruction.

SUMMARY OF THE INVENTION

In view of the drawbacks of the prior art, it would be advantageous to provide a stent capable of delivering a relatively large volume of a beneficial agent to a traumatized site in a vessel while avoiding the numerous problems associated with surface coatings containing beneficial agents, without increasing the effective wall thickness of the stent, and without adversely impacting the mechanical expansion properties of the stent.

It would further be advantageous to have such a stent, which also significantly increases the available depth of the beneficial agent reservoir.

It would also be advantageous to have methods of loading various beneficial agents or combinations of beneficial agents into these deep reservoirs, which provided control over the temporal release kinetics of the agents.

In accordance with one aspect of the invention, an expandable medical device includes a plurality of elongated struts, said plurality of elongated struts joined together to form a substantially cylindrical device which is expandable from a cylinder having a first diameter to a cylinder having a second diameter, said plurality of struts each having a strut width in a circumferential direction and a strut thickness in a radial direction, at least one opening in at least one of the plurality of struts, and at least one beneficial agent provided in the at least one opening in a plurality of layers.

In accordance with a further aspect of the present invention, an expandable medical device includes a plurality of elongated struts, said plurality of elongated struts joined together to form a substantially cylindrical device which is expandable from a cylinder having a first diameter to a cylinder having a second diameter, said plurality of struts each having a strut width in a circumferential direction and a strut thickness in a radial direction, at least one opening in at least one of the plurality of struts, and at least one beneficial agent provided in the at least one opening. A shape of the beneficial agent is configured to achieve a desired agent delivery profile.

In accordance with another aspect of the present invention, an expandable medical device for treating cardiac arrhythmias includes an expandable cylindrical device having a plurality of struts, a plurality of openings in the plurality of struts, and a chemically ablative agent provided in the openings. The openings are configured to deliver the chemically ablative agent to tissue surrounding the expandable cylindrical device without permanently trapping any agent in the openings.

In accordance with an additional aspect of the present invention, an expandable medical device for treating cardiac arrhythmias includes an expandable cylindrical device having a plurality of struts, a plurality of openings in the plurality of struts, and an anti-arrhythmic drug and a non-biodegradable carrier provided in the openings. The openings are configured to deliver the anti-arrhythmic drug to tissue surrounding the cylindrical device over an extended time period.

In accordance with another aspect of the present invention, a method of forming an expandable medical device includes providing an expandable medical device with a plurality of struts, said plurality of struts joined together to form a substantially cylindrical device which is expandable from a cylinder having a first diameter to a cylinder having a second diameter, forming at least one opening in at least one of the plurality of struts, and delivering at least one beneficial agent into in the at least one opening in a plurality of layers.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Figure 1:
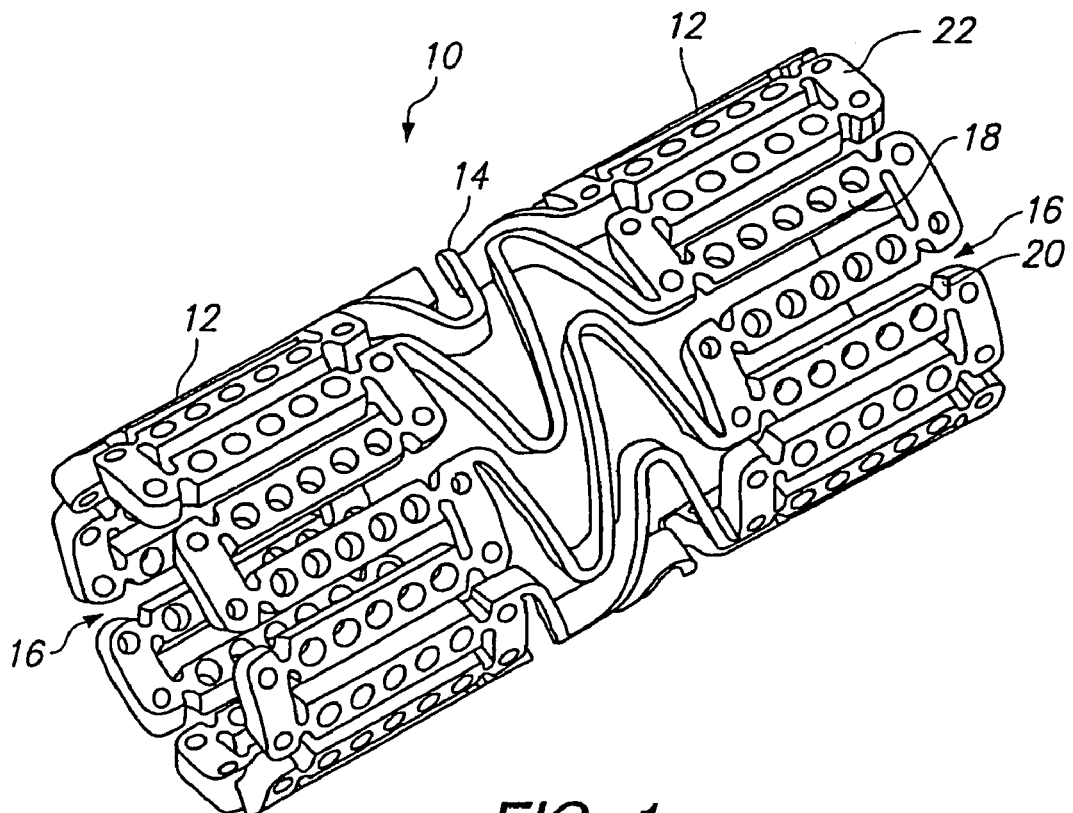
FIG. 1 is a perspective view of a tissue supporting device in accordance with a first preferred embodiment of the present invention.
Figure 2:
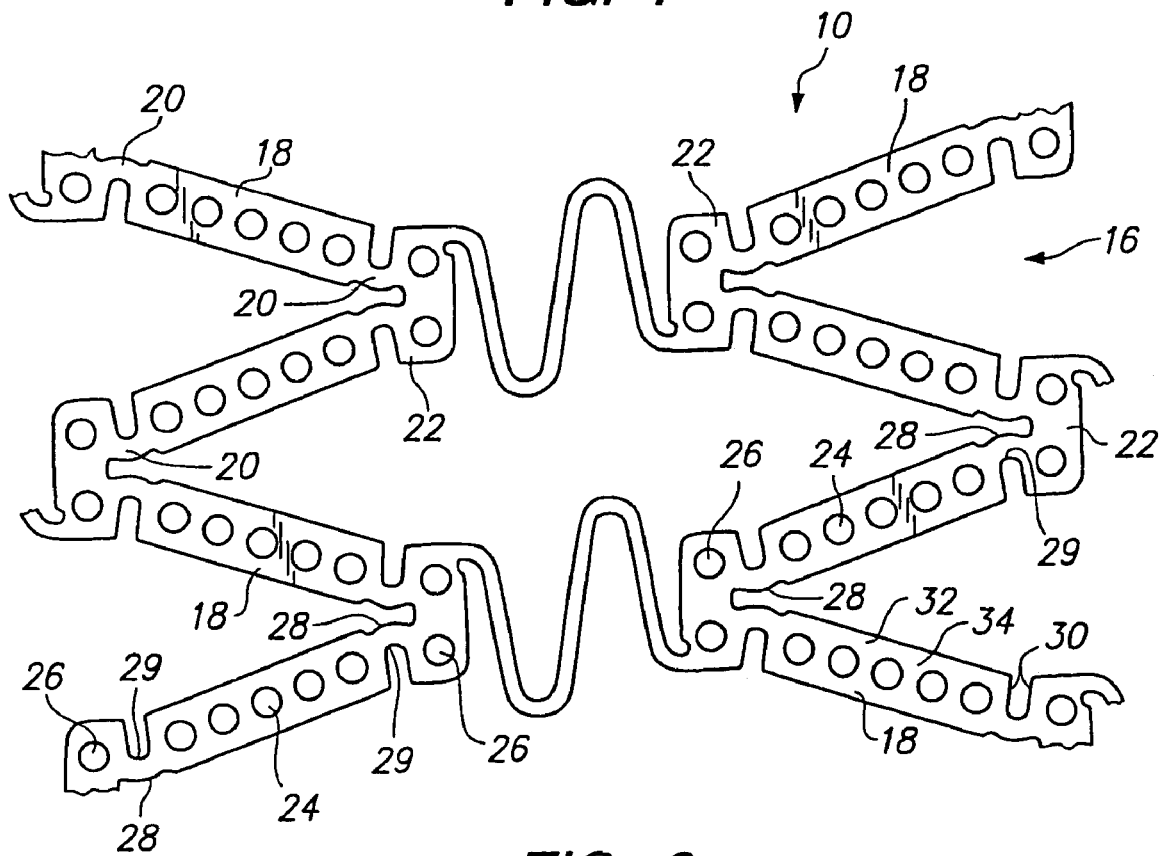
FIG. 2 is an enlarged side view of a portion of the device of FIG. 1.

Referring to FIGS. 1 and 2, a tissue supporting device in accordance with one preferred embodiment of the present invention is shown generally by reference numeral 10. The tissue supporting device 10 includes a plurality of cylindrical tubes 12 connected by S-shaped bridging elements 14. The bridging elements 14 allow the tissue supporting device to bend axially when passing through the tortuous path of the vasculature to the deployment site and allow the device to bend when necessary to match the curvature of a vessel wall to be supported. Each of the cylindrical tubes 12 has a plurality of axial slots 16 extending from an end surface of the cylindrical tube toward an opposite end surface.

Formed between the slots 16 is a network of axial struts 18 and links 22. The struts 18 and links 22 are provided with openings for receiving and delivering a beneficial agent. As will be described below with respect to FIGS. 9-17, the beneficial agent is loaded into the openings in layers or other configurations which provide control over the temporal release kinetics of the agent.

Each individual strut 18 is preferably linked to the rest of the structure through a pair of reduced sections 20, one at each end, which act as stress/strain concentration features. The reduced sections 20 of the struts function as hinges in the cylindrical structure. Since the stress/strain concentration features are designed to operate into the plastic deformation range of generally ductile materials, they are referred to as ductile hinges 20. The ductile hinges 20 are described in further detail in U.S. Pat. No. 6,241,762, which has been incorporated herein by reference.

With reference to the drawings and the discussion, the width of any feature is defined as its dimension in the circumferential direction of the cylinder. The length of any feature is defined as its dimension in the axial direction of the cylinder. The thickness Of any feature is defined as the wall thickness of the cylinder.

The presence of the ductile hinges 20 allows all of the remaining features in the tissue supporting device to be increased in width or the circumferentially oriented component of their respective rectangular moments of inertia—thus greatly increasing the strength and rigidity of these features. The net result is that elastic, and then plastic deformation commence and propagate in the ductile hinges 20 before other structural elements of the device undergo any significant elastic deformation. The force required to expand the tissue supporting device 10 becomes a function of the geometry of the ductile hinges 20, rather than the device structure as a whole, and arbitrarily small expansion forces can be specified by changing hinge geometry for virtually any material wall thickness. The ability to increase the width and thickness of the struts 18 and links 22 provides additional area and depth for the beneficial agent receiving openings.

In the preferred embodiment of FIGS. 1 and 2, it is desirable to increase the width of the individual struts 18 between the ductile hinges 20 to the maximum width that is geometrically possible for a given diameter and a given number of struts arrayed around that diameter. The only geometric limitation on strut width is the minimum practical width of the slots 16 which is about 0.002 inches (0.0508 mm) for laser machining. Lateral stiffness of the struts 18 increases as the cube of strut width, so that relatively small increases in strut width significantly increase strut stiffness. The net result of inserting ductile hinges 20 and increasing strut width is that the struts 18 no longer act as flexible leaf springs, but act as essentially rigid beams between the ductile hinges. All radial expansion or compression of the cylindrical tissue supporting device 10 is accommodated by mechanical strain in the hinge features 20, and yield in the hinge commences at very small overall radial expansion or compression.

The ductile hinge 20 illustrated in FIGS. 1 and 2 is exemplary of a preferred structure that will function as a stress/strain concentrator. Many other stress/strain concentrator configurations may also be used as the ductile hinges in the present invention, as shown and described by way of example in U.S. Pat. No. 6,241,762. The geometric details of the stress/strain concentration features or ductile hinges 20 can be varied greatly to tailor the exact mechanical expansion properties to those required in a specific application.

Although a tissue supporting device configuration has been illustrated in FIG. 1 which includes ductile hinges, it should be understood that the beneficial agent may be contained in openings in stents having a variety of designs including the designs illustrated in U.S. Provisional Patent Application Ser. No. 60/314,360, filed on Aug. 20, 2001 and U.S. patent application Ser. No. 09/948,987, filed on Sep. 7, 2001, which are incorporated herein by reference. The present invention incorporating beneficial agent openings may also be used with other known stent designs.

As shown in FIGS. 1–4, at least one and more preferably a series of openings 24 are formed by laser drilling or any other means known to one skilled in the art at intervals along the neutral axis of the struts 18. Similarly, at least one and preferably a series of openings 26 are formed at selected locations in the links 22. Although the use of openings 24 and 26 in both the struts 18 and links 22 is preferred, it should be clear to one skilled in the art that openings could be formed in only one of the struts and links. Openings may also be formed in the bridging elements 14. In the embodiment of FIGS. 1 and 2, the openings 24, 26 are circular in nature and form cylindrical holes extending through the width of the tissue supporting device 10. It should be apparent to one skilled in the art, however, that openings of any geometrical shape or configuration could of course be used without departing from the scope of the present invention. In addition, openings having a depth less than the thickness of the device may also be used.

The behavior of the struts 18 in bending is analogous to the behavior of an I-beam or truss. The outer edge elements 32 of the struts 18, shown in FIG. 2, correspond to the I-beam flange and carry the tensile and compressive stresses, whereas the inner elements 34 of the struts 18 correspond to the web of an I-beam which carries the shear and helps to prevent buckling and wrinkling of the faces. Since most of the bending load is carried by the outer edge elements 32 of the struts 18, a concentration of as much material as possible away from the neutral axis results in the most efficient sections for resisting strut flexure. As a result, material can be judiciously removed along the axis of the strut so as to form openings 24, 26 without adversely impacting the strength and rigidity of the strut. Since the struts 18 and links 22 thus formed remain essentially rigid during stent expansion, the openings 24, 26 are also non-deforming.

The openings 24, 26 in the struts 18 may promote the healing of the intervention site by promoting regrowth of the endothelial cells. By providing the openings 24, 26 in the struts, 18, the cross section of the strut is effectively reduced without decreasing the strength and integrity of the strut, as described above. As a result, the overall distance across which endothelial cell regrowth must occur is also reduced to approximately 0.0025–0.0035 inches, which is approximately one-half of the thickness of a conventional stent. It is further believed that during insertion of the expandable medical device, cells from the endothelial layer may be scraped from the inner wall of the vessel by the openings 24, 26 and remain therein after implantation. The presence of such endothelial cells would thus provide a basis for the healing of the vessel wall.

The openings 24, 26 are loaded with an agent, most preferably a beneficial agent, for delivery to the vessel wall which the tissue supporting device 10 is supporting.

The terms "agent" and "beneficial agent" as used herein are intended to have their broadest possible interpretation and are used to include any therapeutic agent or drug, as well as inactive agents such as barrier layers or carrier layers. The terms "drug" and "therapeutic agent" are used interchangeably to refer to any therapeutically active substance that is delivered to a bodily conduit of a living being to produce a desired, usually beneficial, effect. The present invention is particularly well suited for the delivery of antiproliferatives (anti-restenosis agents) such as paclitaxel and rapamycin for example, and antithrombins such as heparin, for example.

The beneficial agents used in the present invention include classical small molecular weight therapeutic agents commonly referred to as drugs including all classes of action as exemplified by, but not limited to: antiproliferatives, antithrombins, antiplatelet, antilipid, anti-inflammatory, and anti-angiogenic, vitamins, ACE inhibitors, vasoactive substances, antimitotics, metello-proteinase inhibitors, NO donors, estradiols, anti-sclerosing agents, alone or in combination. Beneficial agent also includes larger molecular weight substances with drug like effects on target tissue sometimes called biologic agents including but not limited to: peptides, lipids, protein drugs, enzymes, oligonucleotides, ribozymes, genetic material, prions, virus, bacteria, and eucaryotic cells such as endothelial cells, monocyte/macrophages or vascular smooth muscle cells to name but a few examples. Other beneficial agents may include but not be limited to physical agents such as microspheres, microbubbles, liposomes, radioactive isotopes, or agents activated by some other form of energy such as light or ultrasonic energy, or by other circulating molecules that can be systemically administered.

The embodiment of the invention shown in FIGS. 1 and 2 can be further refined by using Finite Element Analysis and other techniques to optimize the deployment of the beneficial agent within the openings of the struts and links. Basically, the shape and location of the openings 24, 26 can be modified to maximize the volume of the voids while preserving the relatively high strength and rigidity of the struts 18 with respect to the ductile hinges 20.

Figure 3:
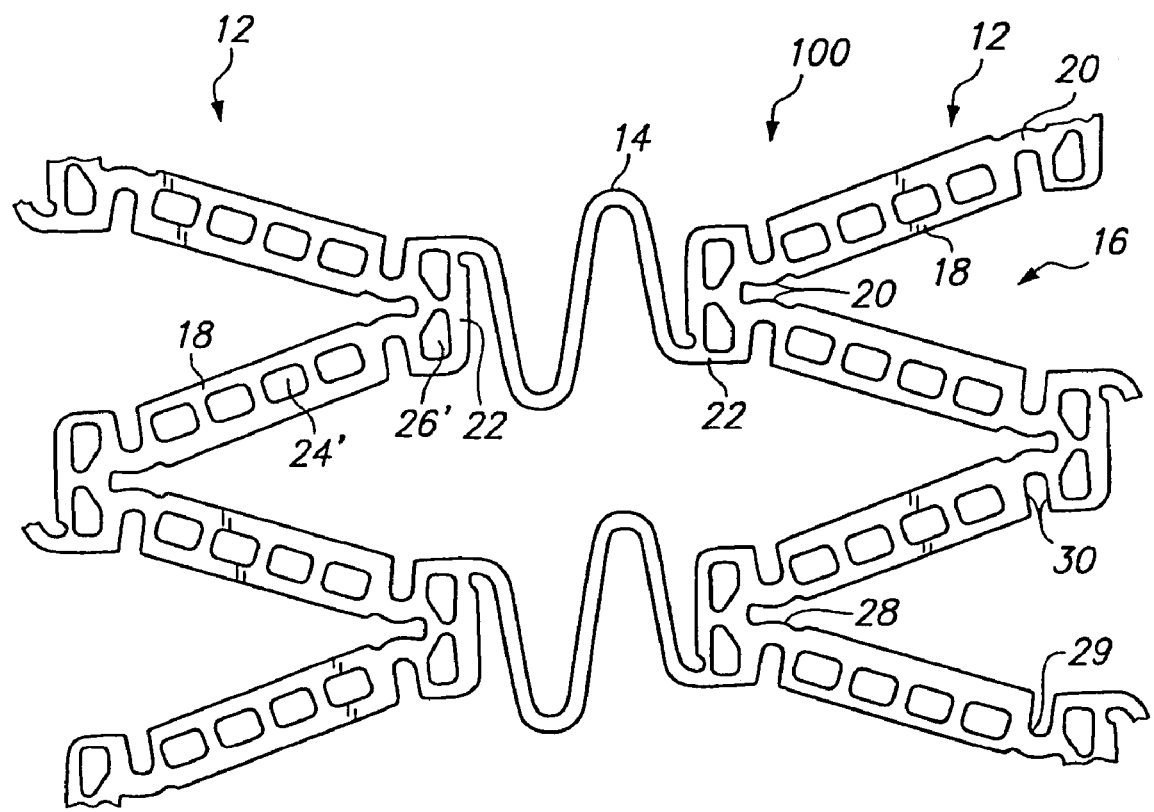
FIG. 3 is an enlarged side view of a tissue supporting device in accordance with a further preferred embodiment of the present invention.

FIG. 3 illustrates a further preferred embodiment of the present invention, wherein like reference numerals have been used to indicate like components. The tissue supporting device 100 includes a plurality of cylindrical tubes 12 connected by S-shaped bridging elements 14. Each of the cylindrical tubes 12 has a plurality of axial slots 16 extending from an end surface of the cylindrical tube toward an opposite end surface. Formed between the slots 16 is a network of axial struts 18 and links 22. Each individual strut 18 is linked to the rest of the structure through a pair of ductile hinges 20, one at each end, which act as stress/strain concentration features. Each of the ductile hinges 20 is formed between an arc surface 28 and a concave notch surface 29.

At intervals along the neutral axis of the struts 18, at least one and more preferably a series of openings 24' are formed by laser drilling or any other means known to one skilled in the art. Similarly, at least one and preferably a series of openings 26' are formed at selected locations in the links 22. Although the use of openings 24', 26' in both the struts 18 and links 22 is preferred, it should be clear to one skilled in the art that openings could be formed in only one of the struts and links. In the illustrated embodiment, the openings 24' in the struts 18 are generally rectangular whereas the openings 26' in the links 22 are polygonal. It should be apparent to one skilled in the art, however, that openings of any geometrical shape or configuration could of course be used, and that the shape of openings 24, 24' may be the same or different from the shape of openings 26, 26', without departing from the scope of the present invention. As described in detail above, the openings 24', 26' may be loaded with an agent, most preferably a beneficial agent, for delivery to the vessel in which the tissue support device 100 is deployed. Although the openings 24', 26'are preferably through openings, they may also be recesses extending only partially through the thickness of the struts and links.

The relatively large, protected openings 24, 24', 26, 26', as described above, make the expandable medical device of the present invention particularly suitable for delivering agents having more esoteric larger molecules or genetic or cellular agents, such as, for example, protein drugs, enzymes, antibodies, antisense oligonucleotides, ribozymes, gene/vector constructs, and cells (including but not limited to cultures of a patient's own endothelial cells). Many of these types of agents are biodegradable or fragile, have a very short or no shelf life, must be prepared at the time of use, or cannot be pre-loaded into delivery devices such as stents during the manufacture thereof for some other reason. The large through-openings in the expandable device of the present invention form protected areas or receptors to facilitate the loading of such an agent either at the time of use or prior to use, and to protect the agent from abrasion and extrusion during delivery and implantation.

The volume of beneficial agent that can be delivered using through openings is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Through openings also decrease the surface area of the beneficial agent bearing compounds to which the vessel wall surface is exposed. For typical devices with beneficial agent openings, this exposure decreases by a factors ranging from about 6:1 to 8:1, by comparison with surface coated stents. This dramatically reduces the exposure of vessel wall tissue to polymer carriers and other agents that can cause inflammation, while simultaneously increasing the quantity of beneficial agent delivered, and improving control of release kinetics.

Figure 4:
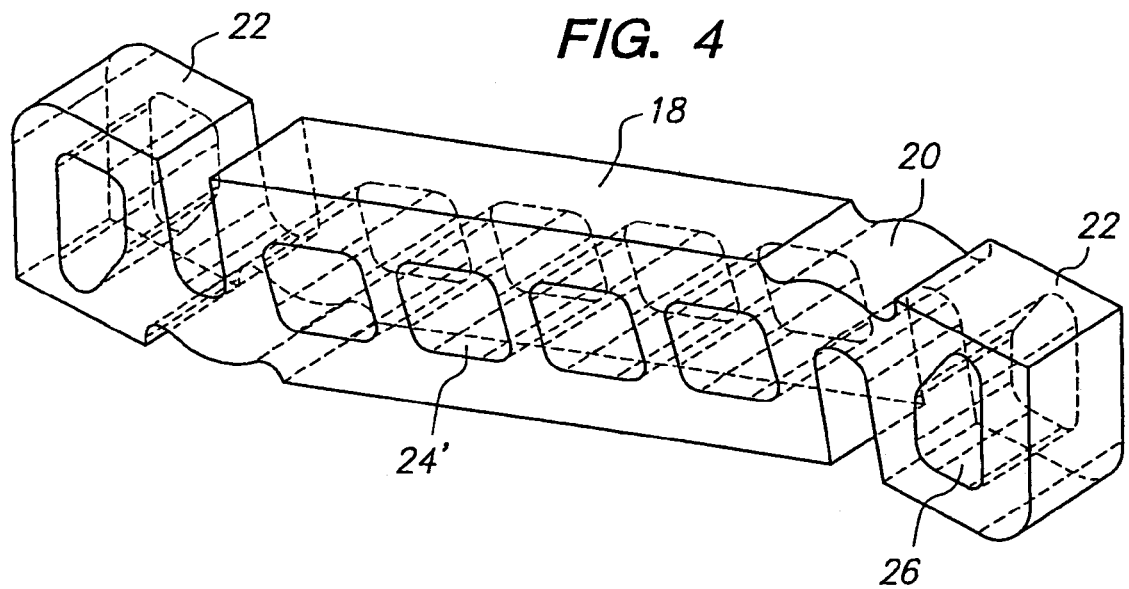
FIG. 4 is an enlarged side view of a portion of the stent shown in FIG. 3.
Figure 5:
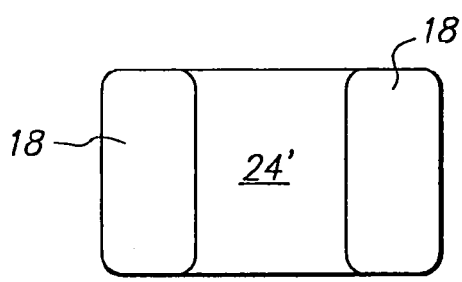
FIG. 5 is an enlarged cross section of an opening.
Figure 6:
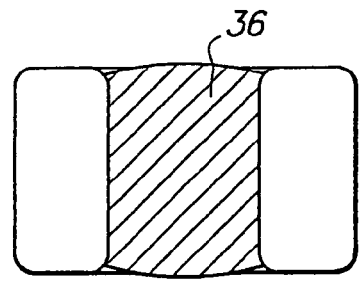
FIG. 6 is an enlarged cross section of an opening illustrating beneficial agent loaded into the opening.
Figure 7:
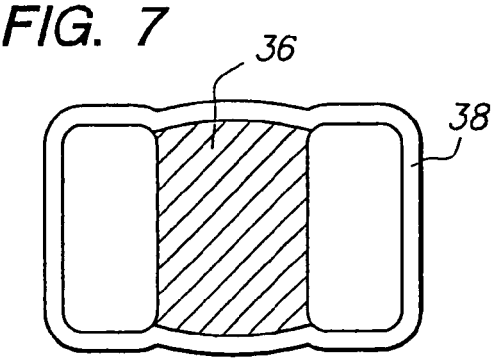
FIG. 7 is an enlarged cross section of an opening illustrating a beneficial agent loaded into the opening and a thin coating of a beneficial agent.
Figure 8:
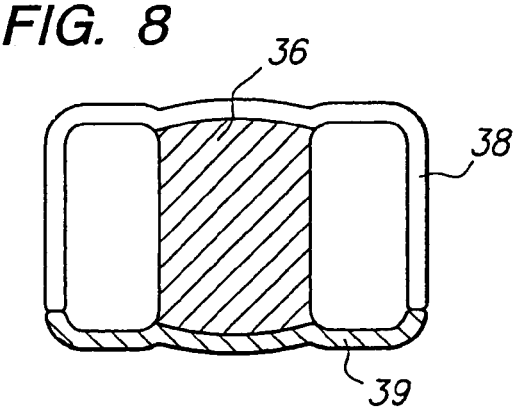
FIG. 8 is an enlarged cross section of an opening illustrating a beneficial agent loaded into the opening and thin coatings of different beneficial agents on different surfaces of the device.

FIG. 4 shows an enlarged view of one of the struts 18 of device 100 disposed between a pair of ductile hinges 20 having a plurality of openings 24'. FIG. 5 illustrates a cross section of one of the openings 24' shown in FIG. 4. FIG. 6 illustrates the same cross section when a beneficial agent 36 has been loaded into the opening 24' of the strut 18. Optionally, after loading the opening 24' and/or the opening 26' with a beneficial agent 36, the entire exterior surface of the stent can be coated with a thin layer of a beneficial agent 38, which may be the same as or different from the beneficial agent 36, as schematically shown in FIG. 7. Still further, another variation of the present invention would coat the outwardly facing surfaces of the stent with a first beneficial agent 38 while coating the inwardly facing surfaces of the stent with a different beneficial agent 39, as illustrated in FIG. 8. The inwardly facing surface of the stent would be defined as at least the surface of the stent which, after expansion, forms the inner passage of the vessel. The outwardly facing surface of the stent would be defined as at least the surface of the stent which, after expansion, is in contact with and directly supports the inner wall of the vessel. The beneficial agent 39 coated on the inner surfaces may be a barrier layer which prevents the beneficial agent 36 from passing into the lumen of the blood vessel and being washed away in the blood stream.

Figure 9:
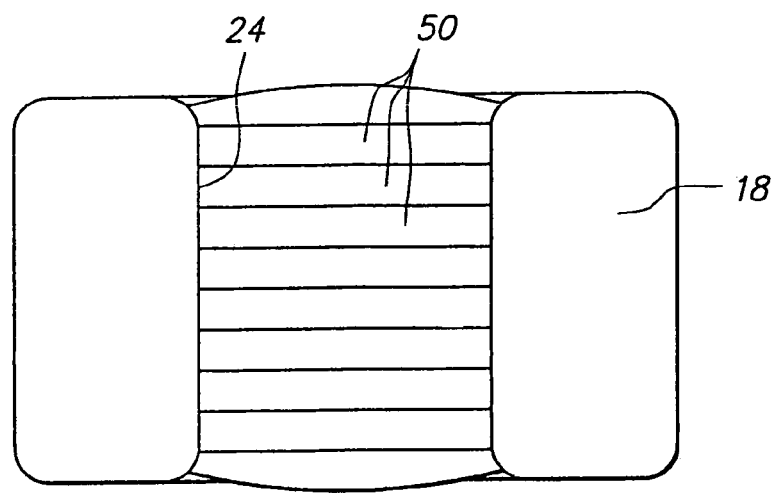
FIG. 9 is an enlarged cross section of an opening illustrating a beneficial agent provided in a plurality of layers.

FIG. 9 shows a cross section of an opening 24 in which one or more beneficial agents have been loaded into the opening 24 in discrete layers 50. One method of creating such layers is to deliver a solution comprising beneficial agent, polymer carrier, and a solvent into the opening and evaporating the solvent to create a thin solid layer of beneficial agent in the carrier. Other methods of delivering the beneficial agent can also be used to create layers. According to another method for creating layers, a beneficial agent may be loaded into the openings alone if the agent is structurally viable without the need for a carrier. The process can then be repeated until each opening is partially or entirely filled.

In a typical embodiment, the total depth of the opening 24 is about 125 to about 140 microns, and the typical layer thickness would be about 2 to about 50 microns, preferably about 12 microns. Each typical layer is thus individually about twice as thick as the typical coating applied to surface-coated stents. There would be at least two and preferably about ten to twelve such layers in a typical opening, with a total beneficial agent thickness about 25 to 28 times greater than a typical surface coating. According to one preferred embodiment of the present invention, the openings have an area of at least $5 \times 10^{-6}$ square inches, and preferably at least $7 \times 10^{-6}$ square inches.

Since each layer is created independently, individual chemical compositions and pharmacokinetic properties can be imparted to each layer. Numerous useful arrangements of such layers can be formed, some of which will be described below. Each of the layers may include one or more agents in the same or different proportions from layer to layer. The layers may be solid, porous, or filled with other drugs or excipients.

FIG. 9 shows the simplest arrangement of layers including identical layers 50 that together form a uniform, homogeneous distribution of beneficial agent. If the carrier polymer were comprised of a biodegradable material, then erosion of the beneficial agent containing carrier would occur on both faces of the opening at the same time, and beneficial agent would be released at an approximately linear rate over time corresponding to the erosion rate of the carrier. This linear or constant release rate is referred to as a zero order delivery profile. Use of biodegradable carriers in combination with through openings is especially useful, to guarantee 100% discharge of the beneficial agent within a desired time without creating virtual spaces or voids between the radially outermost surface of the stent and tissue of the vessel wall. When the biodegradable material in the through openings is removed, the openings may provide a communication between the strut-covered vessel wall and the blood stream. Such communication may accelerate vessel healing and allow the ingrowth of cells and extracellular components that more thoroughly lock the stent in contact with the vessel wall. Alternatively, some through-openings may be loaded with beneficial agent while others are left unloaded. The unloaded holes could provide an immediate nidus for the ingrowth of cells and extracellular components to lock the stent into place, while loaded openings dispense the beneficial agent.

The advantage of complete erosion using the through openings over surface coated stents opens up new possibilities for stent-based therapies. In the treatment of cardiac arrhythmias, such as atrial fibrillation both sustained and paroxysmal, sustained ventricular tachycardia, super ventricular tachycardia including reentrant and ectopic, and sinus tachycardia, a number of techniques under development attempt to ablate tissue in the pulmonary veins or some other critical location using various energy sources, e.g. microwaves, generally referred to as radio-frequency ablation, to create a barrier to the propagation of undesired electrical signals in the form of scar tissue. These techniques have proven difficult to control accurately. A stent based therapy using through openings, biodegradable carriers, and associated techniques described herein could be used to deliver a chemically ablative agent in a specific, precise pattern to a specific area for treatment of atrial fibrillation, while guaranteeing that none of the inherently cytotoxic ablating agent could be permanently trapped in contact with the tissue of the vessel wall.

If, on the other hand, the goal of a particular therapy is to provide a long term effect, beneficial agents located in openings provide an equally dramatic advantage over surface coated devices. In this case, a composition comprising a beneficial agent and a non-biodegradable carrier would be loaded into the through openings, preferably in combination with a diffusion barrier layer as described below. To continue the cardiac arrhythmias example, it might be desirable to introduce a long-term anti-arrhythmic drug near the ostia of the pulmonary veins or some other critical location. The transient diffusion behavior of a beneficial agent through a non-biodegradable carrier matrix can be generally described by Fick's second law:

$$\frac{\partial C_x}{\partial t} = \frac{\partial}{\partial x}\left[D\frac{\partial C_x}{\partial x}\right]$$

Where C is the concentration of beneficial agent at cross section x, x is either the thickness of a surface coating or depth of a through opening, D is the diffusion coefficient and t is time. The solution of this partial differential equation for a through opening with a barrier layer will have the form of a normalized probability integral or Gaussian Error Function, the argument of which will contain the term $$\frac{x}{2\sqrt{Dt}}$$

To compare the time intervals over which a given level of therapy can be sustained for surface coatings vs. through openings, we can use Fick's Second Law to compare the times required to achieve equal concentrations at the most inward surfaces of the coating and opening respectively, i.e. the values of x and t for which the arguments of the Error Function are equal:

$$\frac{x_1}{2\sqrt{Dt_1}} = \frac{x_2}{2\sqrt{Dt_2}} \Rightarrow \frac{x_1^2}{x_2^2} = \frac{t_1}{t_2}$$

The ratio of diffusion times to achieve comparable concentrations thus varies as the square of the ratio of depths. A typical opening depth is about 140 microns while a typical coating thickness is about 5 micron; the square of this ratio is 784, meaning that the effective duration of therapy for through openings is potentially almost three orders of magnitude greater for through openings than for surface coatings of the same composition. The inherent non-linearity of such release profiles can in part be compensated for in the case of through openings, but not in thin surface coatings, by varying the beneficial agent concentration of layers in a through opening as described below. It will be recalled that, in addition to this great advantage in beneficial agent delivery duration, through openings are capable of delivering a 3 to 10 times greater quantity of beneficial agent, providing a decisive overall advantage in sustained therapies. The diffusion example above illustrates the general relationship between depth and diffusion time that is characteristic of a wider class of solid state transport mechanisms.

Beneficial agent that is released to the radially innermost or inwardly facing surface known as the lumen facing surface of an expanded device may be rapidly carried away from the targeted area, for example by the bloodstream, and thus lost. Up to half of the total agent loaded in such situations may have no therapeutic effect due to being carried away by the bloodstream. This is probably the case for all surface coated stents as well as the through opening device of FIG. 9.

Figure 10:
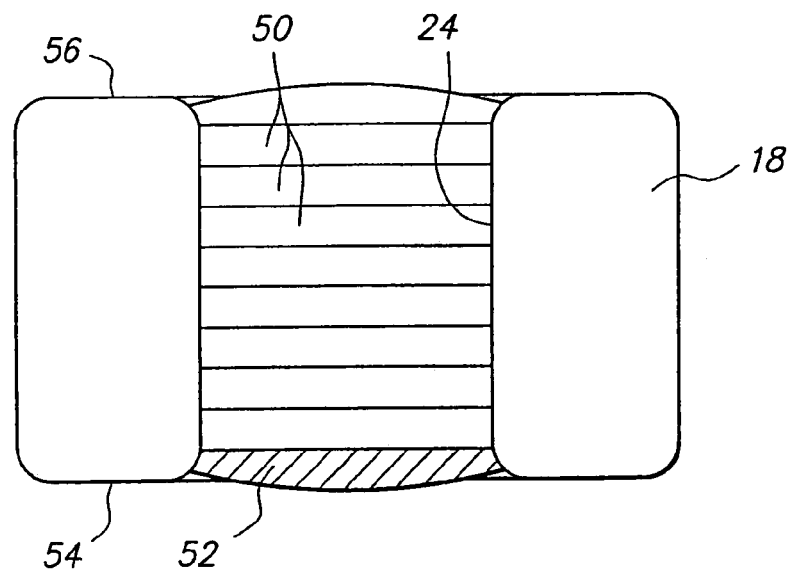
FIG. 10 is an enlarged cross section of an opening illustrating a beneficial agent and a barrier layer loaded into the opening in layers.

FIG. 10 shows a device in which the first layer 52 is loaded into a through opening 24 such that the inner surface of the layer is substantially co-planar with the inwardly facing surface 54 of the cylindrical device. The first layer 52 is comprised of a material called a barrier material which blocks or retards biodegradation of subsequent layers in the inwardly facing direction toward the vessel lumen, and/or blocks or retards diffusion of the beneficial agent in that direction. Biodegradation of other layers or beneficial agent diffusion can then proceed only in the direction of the outwardly facing surface 56 of the device, which is in direct contact with the targeted tissue of the vessel wall. The barrier layer 52 may also function to prevent hydration of inner layers of beneficial agent and thus prevent swelling of the inner layers when such layers are formed of hygroscopic materials. The barrier layer 52 may further be comprised of a biodegradable material that degrades at a much slower rate than the biodegradable material in the other layers, so that the opening will eventually be entirely cleared. Providing a barrier layer 52 in the most inwardly facing surface of a through-opening thus guarantees that the entire load of beneficial agent is delivered to the target area in the vessel wall. It should be noted that providing a barrier layer on the inwardly facing surface of a surface-coated stent without openings does not have the same effect, since the beneficial agent in such a coating cannot migrate through the metal stent to the target area on the outer surface, it simply remains trapped on the inner diameter of the device, again having no therapeutic effect.

Barrier layers can be used to control beneficial agent release kinetics in more sophisticated ways. A barrier layer 52 with a pre-determined degradation time could be used to deliberately terminate the beneficial agent therapy at a pre-determined time, by exposing the underlying layers to more rapid biodegradation from both sides. Barrier layers can also be formulated to be activated by a separate, systemically applied agent. Such systemically applied agent could change the porosity of the barrier layer and/or change the rate of biodegradation of the barrier layer or the bulk beneficial agent carrier. In each case, release of the beneficial agent could be activated by the physician at will by delivery of the systemically applied agent. A further embodiment of physician activated therapy would utilize a beneficial agent encapsulated in micro-bubbles and loaded into device openings. Application of ultrasonic energy from an exterior of the body could be used to collapse the bubbles at a desired time, releasing the beneficial agent to diffuse to the outwardly facing surface of the reservoirs. These activation techniques can be used in conjunction with the release kinetics control techniques described herein to achieve a desired drug release profile that can be activated and/or terminated at selectable points in time.

Figure 11A:
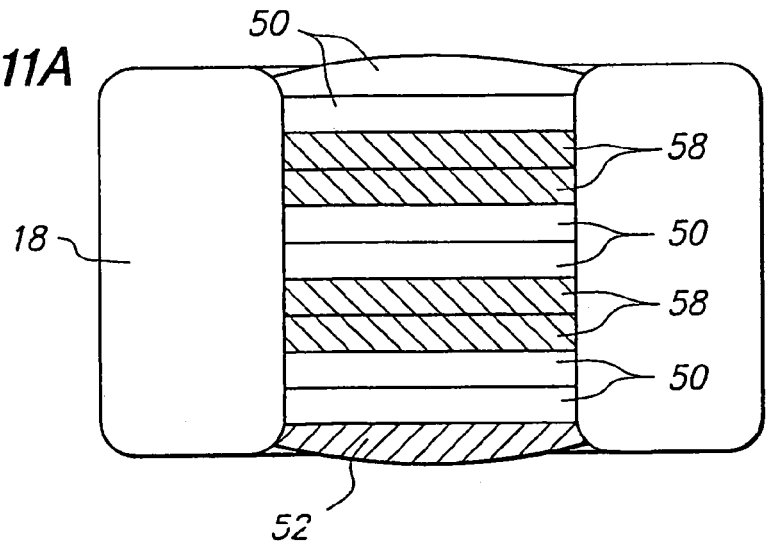
FIG. 11A is an enlarged cross section of an opening illustrating a beneficial agent, a biodegradable carrier, and a barrier layer loaded into the opening in layers.
Figure 11B:
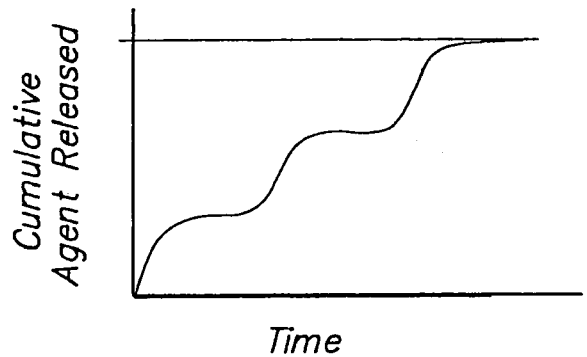
FIG. 11B is a graph of the release kinetics of the device of FIG. 11A.

FIG. 11A shows an arrangement of layers provided in a through opening in which layers 50 of a beneficial agent in a biodegradable carrier material, are alternated with layers 58 of the biodegradable carrier material alone, with no active agent loaded, and a barrier layer 52 is provided at the inwardly facing surface. As shown in the release kinetics plot of FIG. 11B, such an arrangement releases beneficial agent in three programmable bursts or waves achieving a stepped or pulsatile delivery profile. The use of carrier material layers without active agent creates the potential for synchronization of drug release with cellular biochemical processes for enhanced efficacy.

Figure 12:
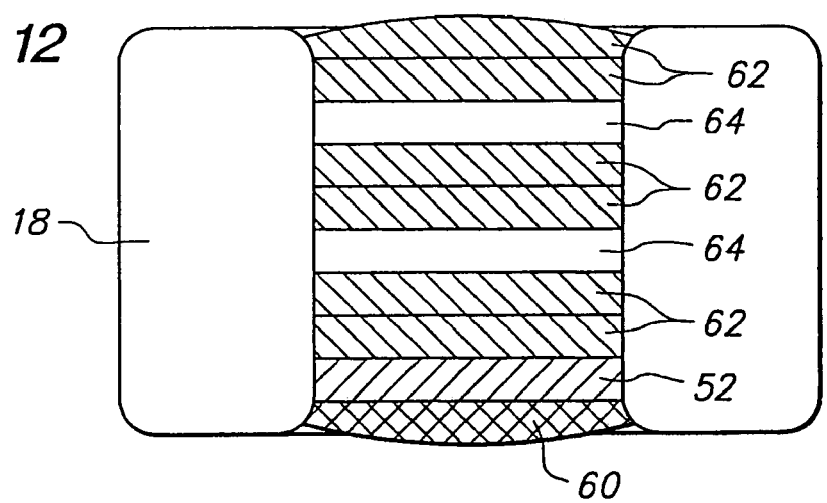
FIG. 12 is an enlarged cross section of an opening illustrating different beneficial agents, carrier, and barrier layers loaded into the opening.

Alternatively, different layers could be comprised of different beneficial agents altogether, creating the ability to release different beneficial agents at different points in time, as shown in FIG. 12. For example, in FIG. 12, a layer 60 of anti-thrombotic agent could be deposited at the inwardly facing surface of the stent, followed by a barrier layer 52 and alternating layers of anti-proliferatives 62 and anti-inflamatories 64. This configuration could provide an initial release of anti-thrombotic agent into the bloodstream while simultaneously providing a gradual release of anti-proliferatives interspersed with programmed bursts of anti-inflammatory agents to the vessel wall. The configurations of these layers can be designed to achieve the agent delivery bursts at particular points in time coordinated with the body's various natural healing processes.

Figure 13:
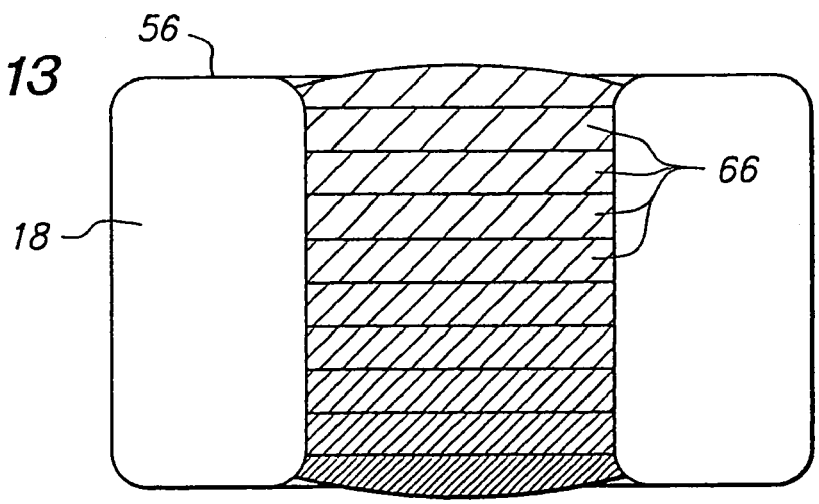
FIG. 13 is an enlarged cross section of an opening illustrating a beneficial agent loaded into the opening in layers of different concentrations.

A further alternative is illustrated in FIG. 13. Here the concentration of the same beneficial agent is varied from layer to layer, creating the ability to generate release profiles of arbitrary shape. Progressively increasing the concentration of agent in the layers 66 with increasing distance from the outwardly facing surface 56, for example, produces a release profile with a progressively increasing release rate, which would be impossible to produce in a thin surface coating.

Another general method for controlling beneficial agent release kinetics is to alter the beneficial agent flux by changing the surface area of drug elution sources as a function of time. This follows from Fick's First Law, which states that the instantaneous molecular flux is proportional to surface area, among other factors:

$$J = D\frac{\partial C}{\partial x} \Rightarrow \frac{\partial N}{\partial t} = AD\frac{\partial c}{\partial x}$$

where $\partial N/\partial t$ is the number of molecules per unit time, A is the instantaneous drug eluting surface area, D is the diffusivity, and C is the concentration. The drug eluting surface area of a surface coated stent is simply the surface area of the stent itself. Since this area is fixed, this method of controlling release kinetics is not available to surface coated devices. Through openings, however, present several possibilities for varying surface area as a function of time.

Figure 14:
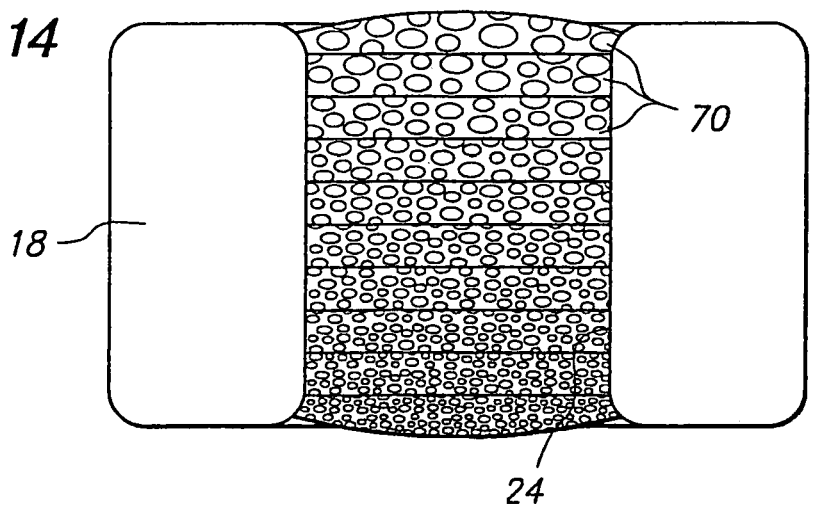
FIG. 14 is an enlarged cross section of an opening illustrating a beneficial agent loaded into the opening in layers of microspheres of different sizes.

In the embodiment of FIG. 14, beneficial agent is provided in the openings 24 in the form of microspheres, particles or the like. Individual layers 70 can then be created that contain these particles. Further, the particle size can be varied from layer to layer. For a given layer volume, smaller particle sizes increase the total particle surface area in that layer, which has the effect of varying the total surface area of the beneficial agent from layer to layer. Since the flux of drug molecules is proportional to surface area, the total drug flux can be adjusted from layer to layer by changing the particle size, and the net effect is control of release kinetics by varying particle sizes within layers.

Figure 15A:
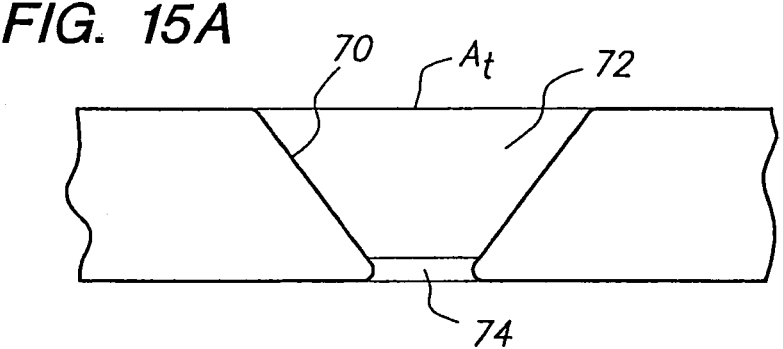
FIG. 15A is an enlarged cross section of a tapered opening illustrating a beneficial agent loaded into the opening.
Figure 15B:
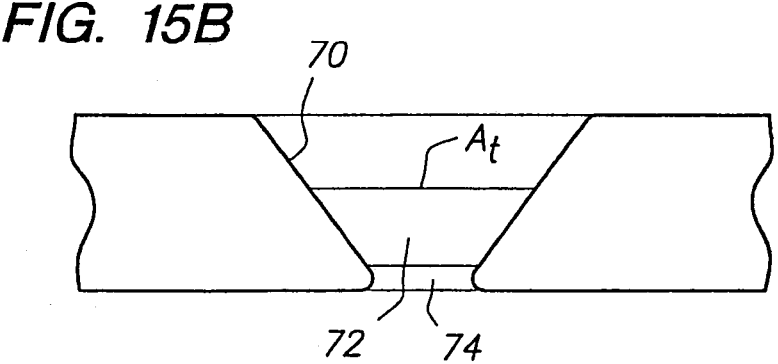
FIG. 15B is an enlarged cross section of the tapered opening of FIG. 15A with the beneficial agent partially degraded.
Figure 15C:
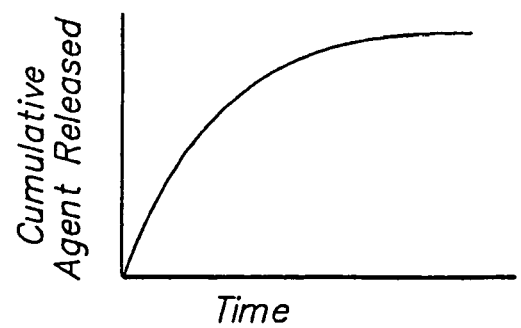
FIG. 15C is a graph of the release kinetics of the device of FIG. 15A.

A second general method for varying drug eluting surface area as a function of time is to change the shape or cross-sectional area of the drug-bearing element along the axis of the opening. FIG. 15A shows an opening 70 having a conical shape cut into the material of the stent itself. The opening 70 may then be filled with beneficial agent 72 in layers as described above or in another manner. In this embodiment, a barrier layer 74 may be provided on the inwardly facing side of the opening 70 to prevent the beneficial agent 72 from passing into the blood stream. In this example, the drug eluting surface area $A_t$ would continuously diminish (from FIG. 15A to FIG. 15B) as the bio-degradable carrier material erodes, yielding the elution pattern of FIG. 15C.

Figure 16A:
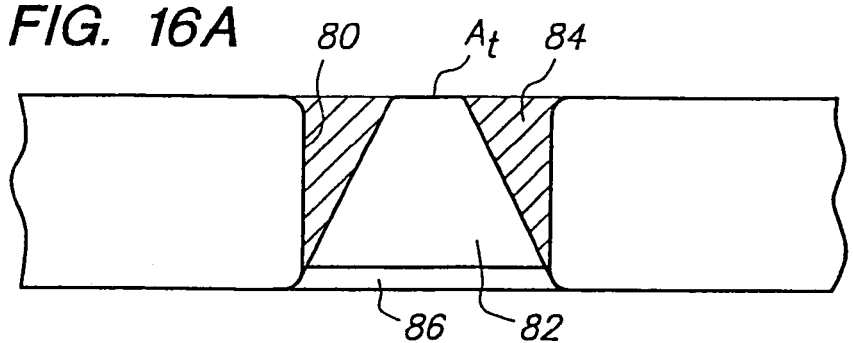
FIG. 16A is an enlarged cross section of an opening illustrating a beneficial agent loaded into the opening in a shape configured to achieve a desired agent delivery profile.
Figure 16B:
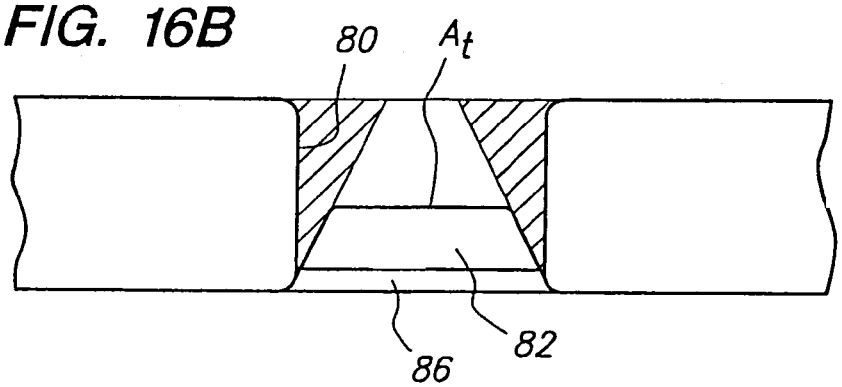
FIG. 16B is an enlarged cross section of the opening of FIG. 16A with the beneficial agent partially degraded.

FIG. 16A shows a simple cylindrical through-opening 80 in which a preformed, inverted cone 82 of beneficial agent has been inserted. The rest of the through opening 80 is then back-filled with a biodegradable substance 84 with a much slower rate of degradation or a non-biodegradable substance, and the inwardly facing opening of the through opening is sealed with a barrier layer 86. This technique yields the opposite behavior to the previous example. The drug-eluting surface area $A_t$ continuously increases with time between FIGS. 16A and 16B, yielding the elution pattern of FIG. 16C.

The changing cross section openings 70 of FIG. 15A and the non-biodegradable backfilling techniques of FIG. 16A may be combined with any of the layered agent embodiments of FIGS. 9–14 to achieve desired release profiles. For example, the embodiment of FIG. 15A may use the varying agent concentration layers of FIG. 13 to more accurately tailor a release curve to a desired profile.

Figure 17A:
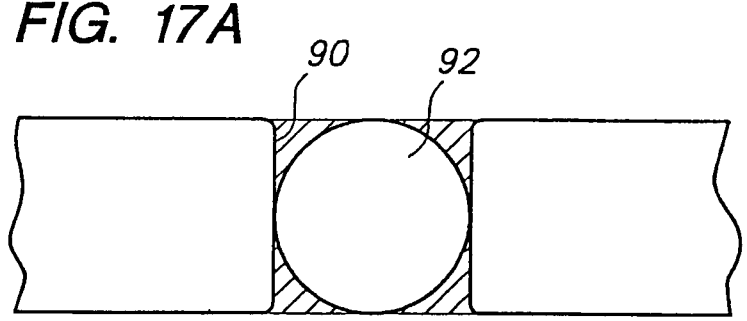
FIG. 17A is an enlarged cross section of an opening illustrating the beneficial agent loaded into the opening and a spherical shape.

The process of preforming the beneficial agent plug 82 to a special shape, inserting in a through opening, and back-filling with a second material can yield more complex release kinetics as well. FIG. 17A shows a through opening 90 in which a spherical beneficial agent plug 92 has been inserted. The resulting biodegradation of the sphere, in which the cross sectional surface area varies as a sinusoidal function of depth, produces a flux density which is roughly a sinusoidal function of time, FIG. 17B. Other results are of course possible with other profiles, but none of these more complex behaviors could be generated in a thin, fixed-area surface coating.

Figure 16C:
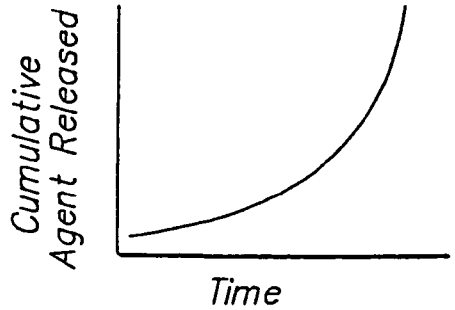
FIG. 16C is a graph of the release kinetics of the device of FIGS. 16A and 16B.
Figure 17B:
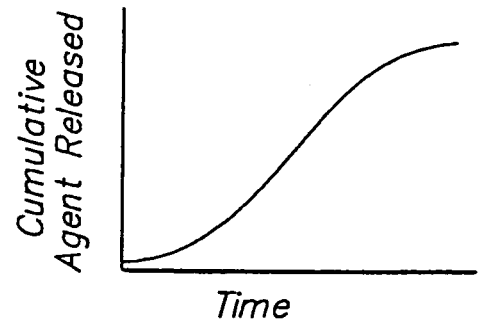
FIG. 17B is a graph of the release kinetics of the device of FIG. 17A.
Figure 18A:
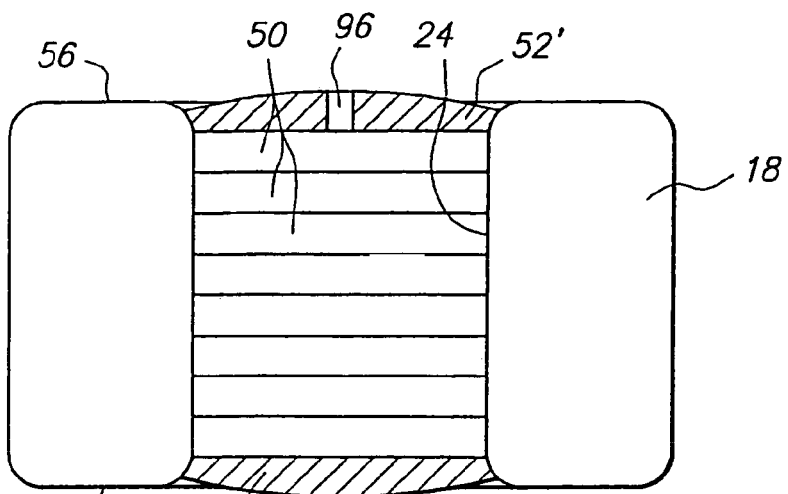
FIG. 18A is an enlarged cross section of an opening illustrating a plurality of beneficial agent layers and a barrier layer with an opening for achieving a desired agent delivery profile.
Figure 18B:
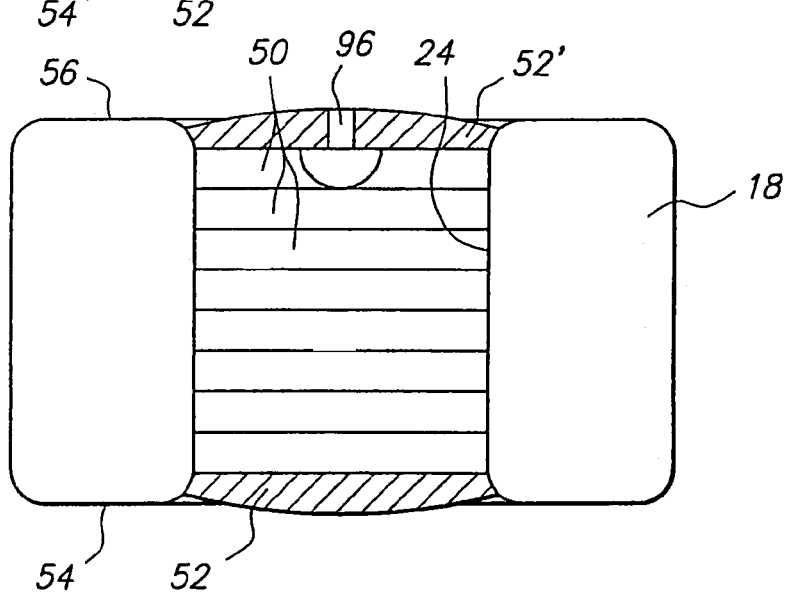
FIG. 18B is an enlarged cross section of the opening of FIG. 18A with the agent layers beginning to degraded.
Figure 18C:
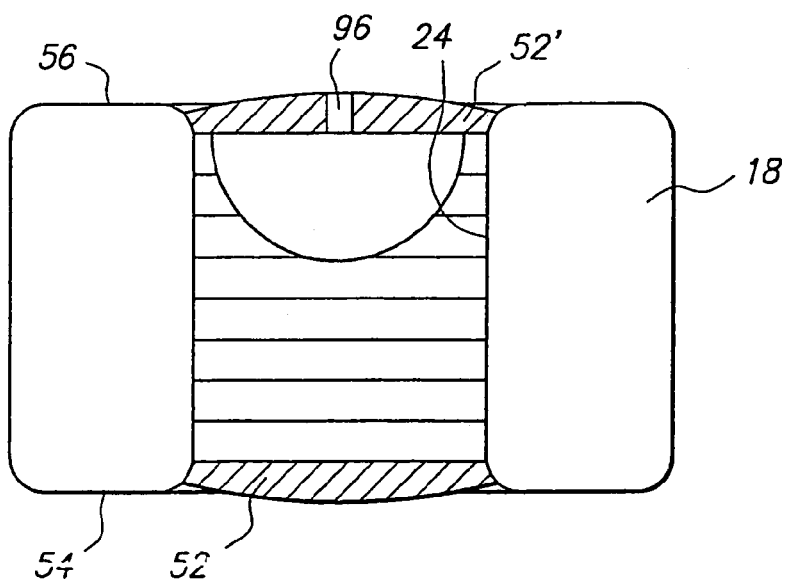
FIG. 18C is an enlarged cross section of the opening of FIG. 18A with the agent layers further degraded.

An alternative embodiment of FIGS. 18A-18C use a barrier layer 52' with an opening 96 to achieve the increasing agent release profile of FIG. 16C. As shown in FIG. 18A, the opening 24 is provided with an inner barrier layer 52 and multiple beneficial agent layers 50 as in the embodiment of FIG. 10. An additional outer barrier layer 52' is provided with a small hole 96 for delivery of the agent to the vessel wall. As shown in FIGS. 18B and 18C, the beneficial agent containing layers 50 degrade in a hemispherical pattern resulting in increasing surface area for agent delivery over time and thus, an increasing agent release profile.

Figure 19:
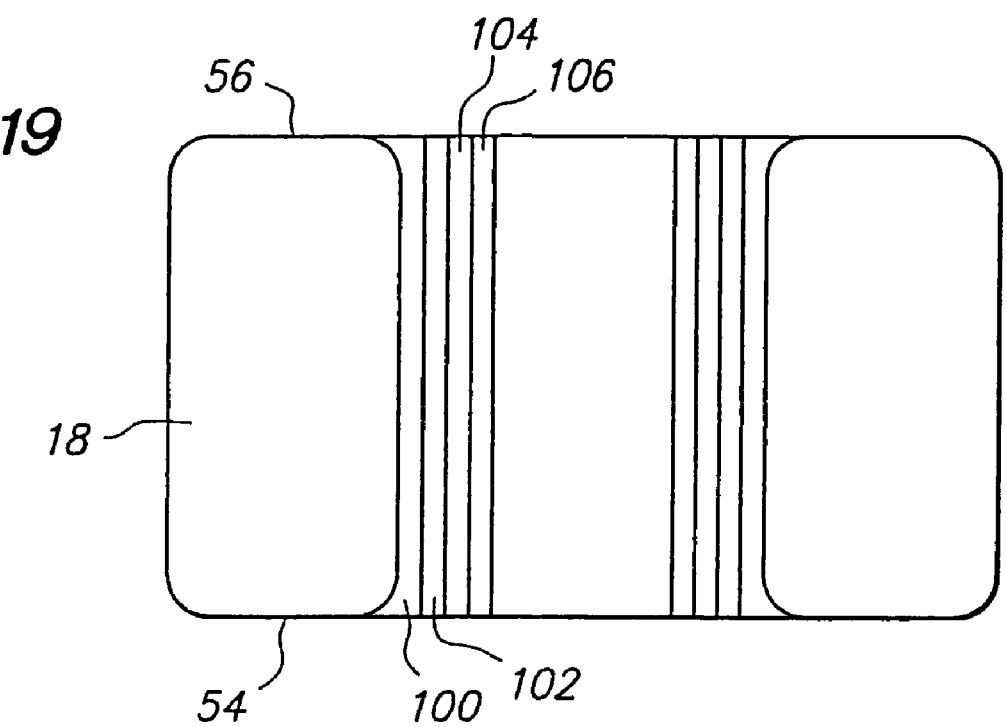
FIG. 19 is an enlarged cross section of an opening illustrating a plurality of cylindrical beneficial agent layers.

FIG. 19 illustrates an alternative embodiment in which an opening in the tissue supporting device is loaded with cylindrical layers of beneficial agent. According to one method of forming the device of FIG. 19, the entire device is coated with sequential layers 100, 102, 104, 106 of beneficial agent. The interior surface 54 and exterior surface 56 of the device are then stripped to remove the beneficial agent on these surfaces leaving the cylindrical layers of beneficial agent in the openings. In this embodiment, a central opening remains after the coating layers have been deposited which allows communication between the outer surface 56 and inner surface 54 of the tissue supporting device.

In the embodiment of FIG. 19, the cylindrical layers are eroded sequentially. This can be used for pulsatile delivery of different beneficial agents, delivery of different concentrations of beneficial agents, or delivery of the same agent. As shown in FIG. 19, the ends of the cylindrical layers 100, 102, 104, 106 are exposed. This results in a low level of erosion of the underlying layers during erosion of an exposed layer. Alternatively, the ends of the cylindrical layers may be covered by a barrier layer to prevent this low level continuous erosion. Erosion rates of the cylindrical layers may be further controlled by contouring the surfaces of the layers. For example, a ribbed or star-shaped pattern may be provided on the radially inner layers to provide a uniform surface area or uniform erosion rate between the radially inner layers and the radially outer layers. Contouring of the surfaces of layers may also be used in other embodiments to provide an additional variable for controlling the erosion rates.

While the invention has been described in detail with reference to the preferred embodiments thereof, it will be apparent to one skilled in the art that various changes and modifications can be made and equivalents employed, without departing from the present invention.

The invention claimed is:

1. A method of forming an expandable medical device comprising:
   (a) forming a substantially cylindrical expandable medical device body formed of a plurality of struts with a plurality of through openings in the plurality of struts;
   (b) forming a first solution of a first beneficial agent, first polymer carrier, and a first solvent;
   (c) delivering the first solution into the openings;
   (d) evaporating the first solvent to form a solid layer of first beneficial agent and first carrier;
   (e) repeating steps (c) and (d); and
   (f) forming a second solution of a second beneficial agent, a second polymer carrier, and a second solvent and delivering the second solution into the openings on top of the layers of first beneficial agent, wherein the second beneficial agent is different from the first beneficial agent.

2. The method of claim 1, wherein the first beneficial agent is an active drug.

3. The method of claim 1, wherein the first beneficial agent is an anti-proliferative.

4. The method of claim 1, wherein the first beneficial agent is an anti-inflammatory.

5. The method of claim 1, wherein the first beneficial agent is an antirestenotic.

6. The method of claim 1, wherein the first beneficial agent is a protein drug.

7. The method of claim 1, wherein the first beneficial agent is an anti thrombin.

8. The method of claim 1, wherein the first beneficial agent is an anti-platelet.

9. The method of claim 1, wherein the first beneficial agent is paclitaxel.

10. The method of claim 1, wherein the first beneficial agent is rapamycin.

11. The method of claim 1, wherein the first beneficial agent is heparin.

12. The method of claim 1, wherein the first beneficial agent is an anti-thrombotic and the second beneficial agent is an anti-proliferative.

13. The method of claim 1, wherein the first beneficial agent is an anti-proliferative and the second beneficial agent is an anti-inflammatory.

14. The method of claim 1, wherein the first and second beneficial agents are arranged to be delivered on a first side of the device body.

15. The method of claim 1, further comprising forming a third solution of a third solvent and a third polymer and delivering the third solution into the opening to form a barrier layer with the openings.

16. The method of claim 1, wherein the first beneficial agent is deposited in the openings to achieve a first release profile and the second beneficial agent is deposited in the openings to achieve a second release profile different from the first release profile.

17. The method of claim 1, wherein a thickness of the layers is 2 µm to 1 µm.

18. The method of claim 1, wherein an area of the openings is at least 0.0032 mm².

19. The method of claim 1, wherein a total depth of the openings is 125 µm to 140 µm.

* * * * *